US011076771B2

(12) United States Patent
Allec et al.

(10) Patent No.: US 11,076,771 B2
(45) Date of Patent: Aug. 3, 2021

(54) SYSTEMS AND METHODS FOR DETERMINING PHYSIOLOGICAL SIGNALS USING AMBIENT LIGHT

(71) Applicant: Apple Inc., Cupertino, CA (US)

(72) Inventors: Nicholas Paul Joseph Allec, Menlo Park, CA (US); Joel S. Armstrong-Muntner, San Mateo, CA (US); Chau V. H. Nguyen, San Jose, CA (US)

(73) Assignee: Apple Inc., Cupertino, CA (US)

( * ) Notice: Subject to any disclaimer, the term of this patent is extended or adjusted under 35 U.S.C. 154(b) by 522 days.

(21) Appl. No.: 15/713,022

(22) Filed: Sep. 22, 2017

(65) Prior Publication Data

US 2018/0078151 A1    Mar. 22, 2018

Related U.S. Application Data

(60) Provisional application No. 62/398,311, filed on Sep. 22, 2016.

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/0059* (2013.01); *A61B 5/02416* (2013.01);
(Continued)

(58) Field of Classification Search
None
See application file for complete search history.

(56) References Cited

U.S. PATENT DOCUMENTS

| 5,483,261 A | 1/1996 | Yasutake |
| 5,488,204 A | 1/1996 | Mead et al. |

(Continued)

FOREIGN PATENT DOCUMENTS

| JP | 2000-163031 A | 6/2000 |
| JP | 2002-342033 A | 11/2002 |

(Continued)

OTHER PUBLICATIONS

Jimenez, L. et al. (2013) "Extracting Heart Rate and Respiration Rate Using a Cell Phone Camera," located at: http://dreuarchive.cra.org/2013/Jimenez/documents/EXTRACTING%20HEART%20RATE%20AND%20RESPIRATION%20RATE%20USING%20A%20CELL%20PHONE%20CAMERA.pdf, six pages.

(Continued)

*Primary Examiner* — Michael R Bloch
(74) *Attorney, Agent, or Firm* — Brownstein Hyatt Farber Schreck, LLP

(57) ABSTRACT

This relates to systems and methods for determining one or more physiological signals of a user using ambient light. The systems and methods can include one or more light sensors configured to measure light that has interacted with a user and one or more light sensors configured to measure ambient light. The gain of the one or more light sensors can be adjusted based on the levels of measured ambient light. For example, the gain of the one or more light sensors can be increased when ambient light levels are low (e.g., a low light environment), or the gain of the one or more light sensors can be decreased when ambient light levels are high (e.g., a bright light environment). In some examples, the systems can include a variable opacity element whose transmission properties (e.g., opacity and/or selected one or more wavelengths to pass through) can be varied.

15 Claims, 16 Drawing Sheets

(51) Int. Cl.
    *A61B 5/1455*     (2006.01)
    *A61B 5/024*     (2006.01)

(52) U.S. Cl.
    CPC ........ *A61B 5/02438* (2013.01); *A61B 5/1455* (2013.01); *A61B 5/681* (2013.01); *A61B 5/6801* (2013.01); *A61B 5/6802* (2013.01); *A61B 5/6898* (2013.01); *A61B 5/7225* (2013.01); *A61B 2560/0242* (2013.01); *A61B 2562/0233* (2013.01)

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,026,602 B2 | 4/2006 | Dausch |
| 7,184,064 B2 | 2/2007 | Zimmerman et al. |
| 7,663,607 B2 | 2/2010 | Hotelling et al. |
| 8,479,122 B2 | 7/2013 | Hotelling et al. |
| 2006/0197753 A1 | 9/2006 | Hotelling |
| 2008/0226137 A1* | 9/2008 | Benaron ............... G06K 9/0012 382/115 |
| 2011/0245637 A1* | 10/2011 | McKenna ............ A61B 5/6826 600/310 |
| 2012/0197137 A1 | 8/2012 | Jeanne et al. |
| 2012/0271121 A1* | 10/2012 | Della Torre ........... A61B 5/024 600/301 |
| 2014/0073486 A1* | 3/2014 | Ahmed ............... A61B 5/02405 482/9 |
| 2014/0142403 A1 | 5/2014 | Brumback et al. |
| 2014/0273858 A1* | 9/2014 | Panther ................ A61B 5/0002 455/41.2 |
| 2014/0288435 A1 | 9/2014 | Richards et al. |
| 2014/0303454 A1 | 10/2014 | Clifton et al. |
| 2015/0057967 A1* | 2/2015 | Albinali ................ A61B 5/1118 702/150 |
| 2015/0148636 A1 | 5/2015 | Benaron |
| 2016/0324432 A1* | 11/2016 | Ahmed ................ A61B 5/0022 |

FOREIGN PATENT DOCUMENTS

| | | |
|---|---|---|
| WO | WO-2011/104714 A1 | 9/2011 |
| WO | WO-2011/152955 A2 | 12/2011 |
| WO | WO-2014/039567 A1 | 3/2014 |
| WO | WO-2014/125250 A1 | 8/2014 |
| WO | WO-2016/176218 A1 | 11/2016 |
| WO | WO-2018/057937 A1 | 3/2018 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Meredith, D. J. et al. (2012). "Photoplethysmographic derivation of respiratory rate: a review of relevant physiology," Journal of Medical Engineering and Technology, pp. 60-66.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

International Search Report dated Dec. 5, 2017, for PCT Application No. PCT/US2017/053029, six pages.

\* cited by examiner

SYSTEMS AND METHODS FOR DETERMINING PHYSIOLOGICAL SIGNALS USING AMBIENT LIGHT

CROSS-REFERENCE TO RELATED APPLICATIONS

This application claims priority to U.S. Provisional Patent Application Ser. No. 62/398,311, filed Sep. 22, 2016, which is hereby incorporated by reference in its entirety.

FIELD OF THE DISCLOSURE

This relates to systems and methods for determining one or more physiological signals of a user using ambient light.

BACKGROUND OF THE DISCLOSURE

Optical sensing of physiological parameters can include using one or more light emitters to illuminate the skin of a user and one or more detectors to sense the light after it has interacted with the skin. For example, photodetectors may sense light that has been transmitted through and/or reflected from the skin of a user to determine various cardiovascular parameters (e.g., heart rate), respiratory parameters (e.g., breathing rate), and/or other cardiopulmonary parameters (e.g., oxygenation levels). In some instances, the detected light can be used by a device to generate a photoplethysmogram (PPG) signal, which can use optical measurement information to determine an estimate of the blood flow changes in an organ of interest (e.g., skin).

In some instances, the device can draw energy from a power source to activate the light emitter(s). Drawing energy may deplete the life of the battery, which may require frequent battery charging and/or replacement by the user. Wearable devices, for example, that require frequent charging and/or battery replacement can be cumbersome for some users. Accordingly, a device configured to measure PPG signals while limiting the activation of light emitter(s), thereby reducing power consumption, may be desired.

In some instances, the ambient light (e.g., sunlight) can include a large amount of light (e.g., high intensity of photons) that may reach the sensing device and can mask the PPG signal. The sensing device may increase the source output such that the dynamic range for the PPG signal meets a certain criteria. For example, the sensing device may increase the output intensity of the light sources. In some instances, the large amount of light can cause sensor saturation and may lead to loss of measurable signal.

SUMMARY OF THE DISCLOSURE

This relates to systems and methods for determining one or more physiological signals of a user using ambient light. The systems and methods can include one or more light sensors configured to measure light that has interacted with a user and one or more light sensors configured to measure ambient light. The gain of the one or more light sensors can be adjusted based on the levels of measured ambient light. For example, the gain of the one or more light sensors can be increased when ambient light levels are low (e.g., a low light environment), or the gain of the one or more light sensors can be decreased when ambient light levels are high (e.g., a bright light environment). In some examples, the systems can include a variable opacity element whose transmission properties (e.g., opacity and/or selected one or more wavelengths to pass through) can be varied.

DETAILED DESCRIPTION

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

This relates to systems and methods for determining one or more physiological signals of a user using ambient light. The systems and methods can include one or more light sensors (e.g., physiological data sensor(s)) configured to measure light that has interacted with a user and one or more light sensors (e.g., ambient light sensor(s)) configured to measure ambient light. The gain of the physiological data sensor(s) can be adjusted based on the levels of measured ambient light. For example, the gain of the one or more light sensors can be increased when ambient light levels are low (e.g., a low light environment), or the gain of the one or more light sensors can be decreased when ambient light levels are high (e.g., a bright light environment). In some examples, the systems can include a variable opacity element whose transmission properties (e.g., opacity and/or selected one or more wavelengths to pass through) can be varied.

Figure 1:
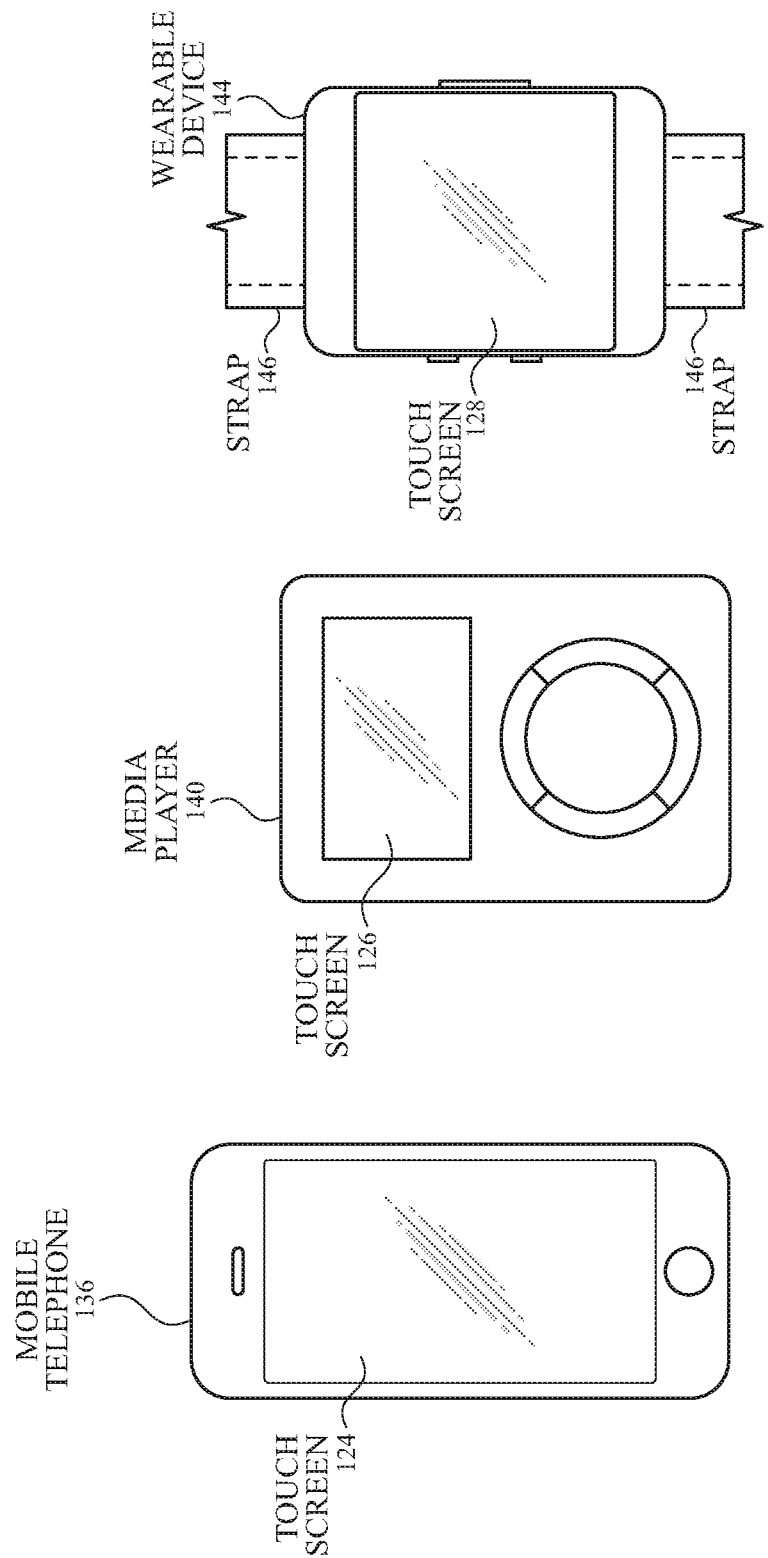
FIGS. 1A-1C illustrate systems in which examples of the disclosure can be implemented.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the PPG light sensors, ambient light sensors (ALS), and configurations and methods for operating thereof, as will be disclosed.

Figure 2:
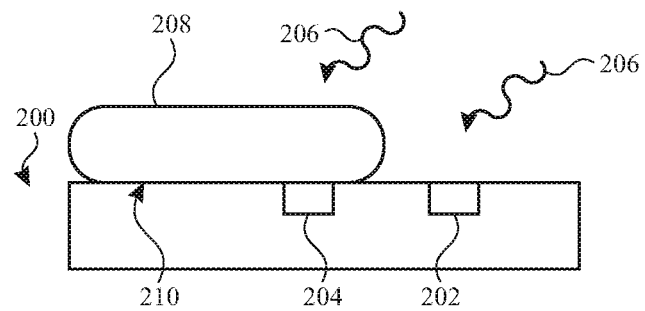
FIG. 2 illustrates a cross-sectional view of an exemplary configuration including a plurality of light sensors located on a top surface of a device according to examples of the disclosure.

FIG. 2 illustrates a cross-sectional view of an exemplary configuration including a plurality of light sensors located on a top surface of a device according to examples of the disclosure. Device 200 can include top surface 210 configured to face user 208. Device 200 can include a first light sensor 202 and a second light sensor 204. The user 208 can position a portion of their body (e.g., a finger) over the second light sensor 204. Ambient light 206 can be detected by first light sensor 202. Ambient light 206 can also propagate through user 208. Second light sensor 204 can detect ambient light that has interacted with user 208. For example, ambient light can be absorbed, reflected, and/or scattered within user 208, and light detected by the second light sensor 204 can be correlated with one or more physiological parameters of interest. The movement of blood (e.g., blood flow) through the user 208 can be detected by the second light sensor as light fluctuates. Pulsatile blood flow can modulate light 206 in a periodic fashion, and the blood flow rate can be computed based on the modulated light. In some examples, the housing of device 200 can include optically transparent regions (e.g., openings or regions made of light-transmitting materials) that can be co-located with the locations of the light sensors (e.g., light sensor 202 and light sensor 204). In some examples, one or more of the light sensors can be embedded within the thickness of the housing.

In some examples, at least one light sensor (e.g., light sensor 204) can have adjustable gain. The gain of the light sensor can be adjusted based on the ambient light levels. In some examples, device 200 can be configured such that light sensor 202 can detect ambient light levels and light sensor 204 can detect light with physiological relevant information. The gain of light sensor 204 can be adjusted according to the ambient light levels detected by light sensor 202.

In some examples, the gain of light sensor 204 can be adjusted (e.g., increased) when ambient light levels are low to increase the sensitivity of light sensor 204, and as a result, can increase the signal strength. With increased signal strength, detection of light in the responsive operation range of light sensor 204 can be enhanced for improved measurement accuracy.

In some examples, the gain of light sensor 204 can be adjusted (e.g., decreased) to avoid saturating light sensor 204 when ambient light levels are high. In some examples, a controller can adjust the gain of a light sensor to increase the detection sensitivity to one or more wavelengths (over other wavelengths).

In some examples, ambient light sensing can be used to prompt the user to perform an action. For example, the user may be located in an environment with low-light conditions, which may not be suitable for obtaining a physiological measurement. The device can detect when the ambient light levels are low and can prompt the user to move to a region with an appropriate amount of ambient light (e.g., indoors, outdoors, or out of the shade) and/or to adjust the environmental lighting (e.g., turn off or turn on a table lamp).

In some examples, the ambient light detected by light sensor 202 can be used to remove unwanted environmental noise from the signal(s) generated by light sensor 204. Having a device capable of detecting ambient noise in the environment can allow for enhanced measurement accuracy. In some examples, the controller can be configured to remove ambient noise from known sources in the environment. The known sources can have one or more characteristics. For example, a lamp light source can contribute to ambient noise by way of harmonic peaks. Examples of the disclosure can include one or more algorithms for removing harmonic peaks, dynamic band pass filtering, etc. Some sources can contribute noise at certain frequencies (e.g., 60

Hz), and the controller can be configured to change the measurement frequency in these instances where the ambient noise can be included in the frequency spectrum. In some examples, the controller can configure the ambient light sensor to have a different measurement frequency (e.g., higher frequency) than the physiological light sensor.

Device 200 can include a controller in communication with the adjustable gain light sensor. The light sensor or photodetector can include a photodiode, photodiode array (PDA), CCD light sensor, CMOS light sensor, and the like. The controller can be configured to adjust the gain of the light sensor based on whether the light sensor signal (i.e., an output voltage or current of the light sensor in response to detected light) is within a predetermined range (e.g., the operating range of the light sensor). The operating range of a light sensor can be the region of the light response curve where the output (e.g., voltage or current) of the light sensor can correspond with light intensity. That is, as the amount of light (e.g., light intensity) incident on the light sensor increase (or decreases), the output response of the light sensor can also increase (or decrease).

Light intensities outside of the operating range of the light sensor may not be reflected in the output of the light sensor. For example, the light sensor may not increase the level of its output signal when the incident light intensity meets or exceeds a pre-determined high threshold. In some instances, the light sensor may not decrease the level of its output signal when the incident light intensity meets or exceeds a pre-determined low threshold. In some examples, the operating range of a light sensor can include a region of the light response curve where the output can be logarithmically related to the light intensity. In some examples, the operating range of a light sensor can be the region of the light response curve where the output can be linearly related, or proportional, to the light intensity. For example, the operating range of a photodiode can be the range of light intensities between a first threshold, where the voltage or current response falls between the noise floor and the saturation limit of the photodiode. The noise floor can be where the voltage or current response of the light sensor may not be functionally distinguishable from noise. The saturation limit can be where the voltage or current response of the light sensor can attain its highest level of output such that further increases in light intensity may not be reflected in increased levels of output.

If the light sensor signal is near the saturation limit of the light sensor, the controller can reduce the gain such that the light sensor response curve can shift to allow the same light intensity to trigger a lower voltage response closer to the mid-point (e.g., between the noise floor and the saturation limit) of the response curve. In some examples, if the light sensor signal is near the noise floor of the light sensor, the controller can increase the gain such that the response curve can shift to allow the same light intensity to trigger a higher voltage response that may be closer to the mid-point (e.g., half way between the noise floor and the saturation limit) of the response curve.

In some examples, when the light levels can fluctuate over time (e.g., in accordance to periodic physiological parameters such as heartbeats or breaths), the average voltage value over time may be considered the DC level of the signal. The controller can adjust the gain of the light sensor based on the value of the DC level of the signal instead of the local minima or maxima of the fluctuating signal (e.g., the AC component of the signal). For example, if the DC level or average value of the voltage or current response of the light sensor is between the noise floor and the saturation limit, even if the fluctuations meet or fall outside of either of the thresholds, the controller may not adjust the gain. In some examples, if any of the peaks or troughs of a fluctuating signal meets or exceeds the noise floor or saturation limit, the controller can adjust the gain of the light sensor such that fluctuations of the light signal are in the operating range.

Figure 3A:
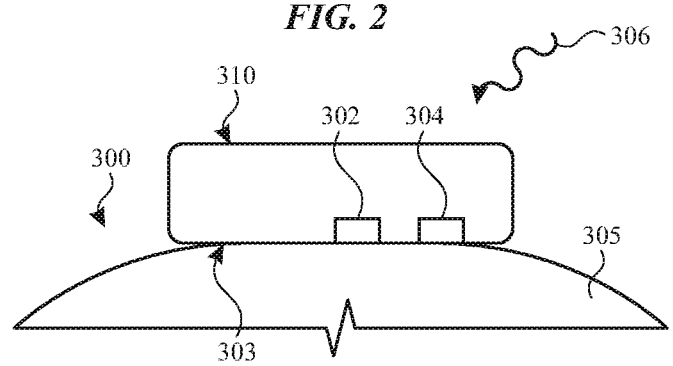
FIGS. 3A-3C illustrate cross-sectional views of exemplary configurations of the light sensors included in a device according to examples of the disclosure.
Figure 3B:
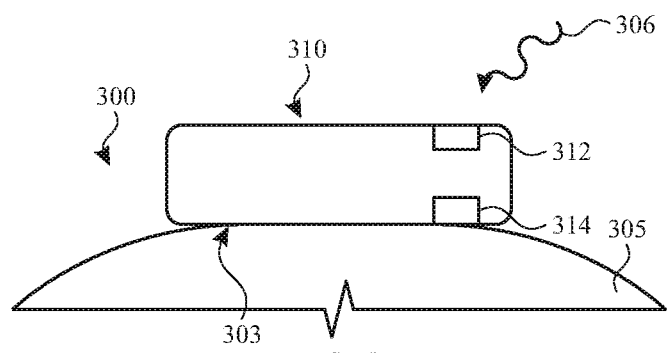
Figure 3C:
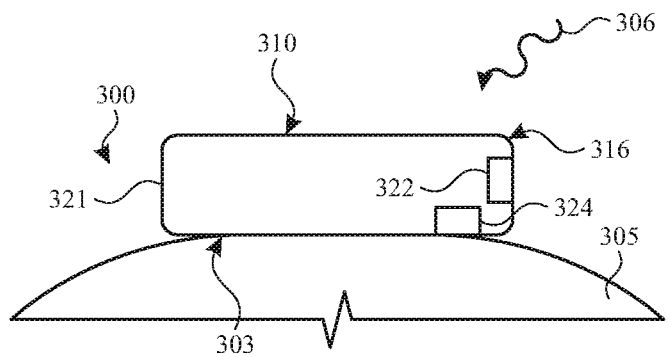

Examples of the disclosure can include multiple configurations of the light sensor(s) relative to each other and/or relative to the surface(s) of the housing of the device. FIGS. 3A-3C illustrate cross-sectional views of exemplary configurations of the light sensors according to examples of the disclosure. For example, as illustrated in FIG. 3A, the light sensors can both be located on the underside of the device. Device 300 can include bottom surface 303, which can be opposite from top surface 310. In some examples, a viewable display or touchscreen can be located on top surface 310. In some examples, the skin of user 305 can contact bottom surface 303. Light sensor 302 and light sensor 304 can be located on the bottom surface 303, where the field-of-view of both light sensors can face user 305. One or both of light sensor 302 and light sensor 304 can have adjustable gain. In some examples, the gain of light sensor 304 can be adjusted according to ambient light detected by light sensor 302.

FIG. 3B illustrates another configuration where the light sensors can be located on opposite sides of the device according to examples of the disclosure. Device 300 can include light sensor 312 and light sensor 314. Light sensor 312 can be located on top surface 310 of device 300, and light sensor 314 can be located on bottom surface 303 of device 300. The field-of-view of light sensor 312 can face ambient light 306, and the field-of-view of light sensor 314 can face user 305. Light sensor 312 can be configured to detect ambient light, while light sensor 314 can be configured to detect light that has interacted with user 305. The gain of light sensor 314 can be adjusted in accordance with the levels of ambient light detected by light sensor 312.

In some examples, one light sensor can be located on one or more sidewalls of the device, as illustrated in FIG. 3C. Device 300 can include sidewall 316 and sidewall 321. In some examples, a sidewall (e.g., sidewall 316 and/or sidewall 321) can run perpendicular to a top surface (e.g., top surface 310) and/or a bottom surface (e.g., bottom surface 303). Device can also include light sensor 322 and light sensor 324. Light sensor 322 can be located on sidewall 316 of device 300, and light sensor 324 can be located on bottom surface 303 of device 300. The field-of-view of light sensor 322 can face at least a portion of ambient light 306, and the field-of-view of light sensor 324 can face user 305. Light sensor 322 can be configured to detect ambient light, while light sensor 324 can be configured to detect light that has interacted with user 305. The gain of light sensor 324 can be adjusted in accordance with the levels of ambient light detected by light sensor 322.

In addition to the configurations illustrated in FIGS. 2 and 3A-3C, examples of the disclosure can include the light sensors located on opposite ends of a device. For example, light sensor 312 can be located on the right portion of the device, and light sensor 314 can be located on the left portion of the device, or vice versa. In some examples, the light sensors can be located along one surface of the housing (e.g., both light sensors can be located along the top or bottom surfaces or sidewalls) or along various surfaces (e.g., one light sensor can be located along a first surface, while another light sensor can be located along a second surface or any of the sidewalls). In some examples, placement of a light sensor can depend on which surface contacts the skin of the user. For example, one light sensor can be located along a tissue-contacting surface, while another light sensor can be along a tissue-inaccessible surface. In some examples, the device can include only one light sensor, and the single light sensor can be located at any of the locations described above and illustrated in FIGS. 2 and 3A-3C.

Examples of the disclosure can include a device that can be a wrist-worn device, phone, smart phone, tablet, mouse or trackpad, keyboard, remote controller (e.g., for a television or a game console), any electronic device with a touch-sensitive surface or display, athletic equipment, and/or automobile control mechanism (e.g., steering wheel). The light sensors can be located within any of the above devices, where the housing can provide optical access to the light sensors at locations where ambient light can be detected and/or location that may be contacted by a user. For example, one or more light sensors can be located on or within a mouse or trackpad. Any surfaces adjacent to the mouse or trackpad can be contacted by a user. A keyboard can include one or more light sensors located on or within one or more keys. Controllers for game consoles and/or televisions can include one or more light sensors on the controller buttons, joystick, trackpad, touch-sensitive surfaces, or the like. In some examples, the device can be a sports instrument, such as a racket, stick, bat, exercise machine (e.g., elliptical machine, treadmill, or stationary bicycle), and one or more of the light sensors can be located on or within the sports instrument. The device can be a steering wheel for a video game or automobile, and one or more of the light sensors can be located on or within regions of the steering wheel, for example, at or near gripping regions of the steering wheel. Although the examples disclosed refer to a wrist-worn or wearable device, examples of the disclosure can include mechanisms and methods that can be used with any of the devices listed above.

Figure 4A:
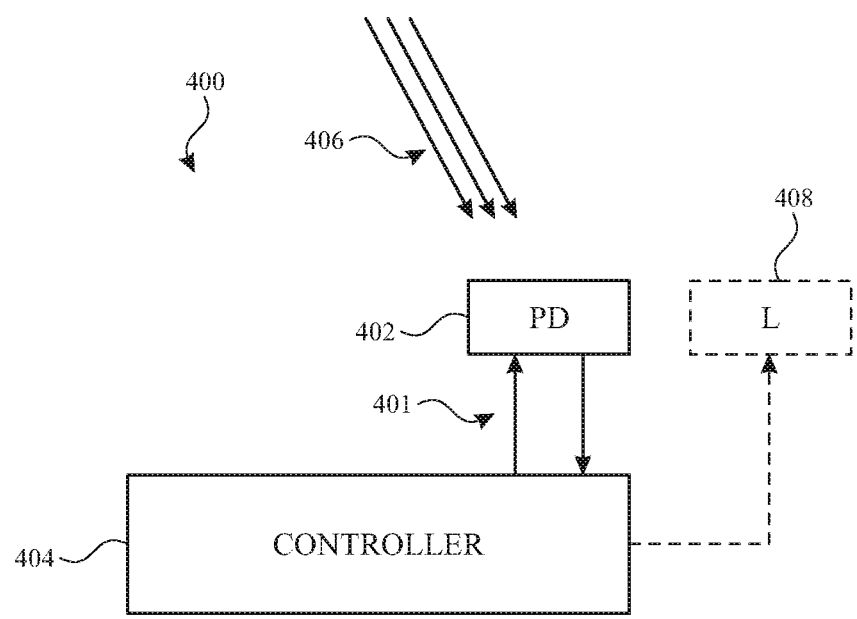
FIGS. 4A-4B illustrate exemplary block diagrams of a device configured for optical sensing of physiological parameters using ambient light according to examples of the disclosure.
Figure 4B:
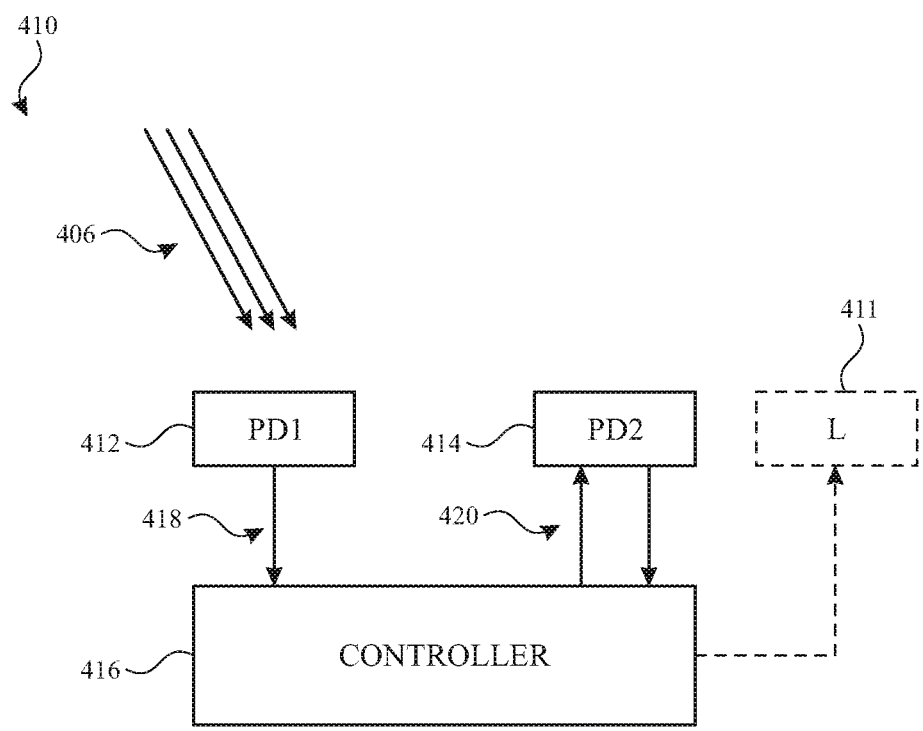

FIGS. 4A-4B illustrate exemplary block diagrams of a device configured for optical sensing of physiological parameters using ambient light according to examples of the disclosure. As illustrated in FIG. 4A, device 400 can include a single light sensor 402 and a controller 404. Controller 404 can be in communication with light sensor 402 via communication channels 401 (which may be wired or wireless). Light sensor 402 can be any of the light sensors described above. Light sensor 402 can be positioned to receive ambient light 406. In some examples, light sensor 402 can be configured to receive light that has interacted with the body (e.g., skin) of a user. For example, the user can place the surface (e.g., surface of a fingertip) of his/her skin over light sensor 402 when he/she wishes to obtain physiological information, including information related to heart rate and/or breathing rate. The detected ambient light signal(s) and/or physiologically related light signal(s) may be transmitted from light sensor 402 to controller 404. The gain of light sensor 402 can be adjusted based on a characteristic (e.g., intensity) of the ambient light signal, the physiologically relevant light signal, or both. For example, if the detected light signals are high (e.g., the DC level of light intensity is within a predetermined margin of or exceeds the saturation level), controller 404 may reduce the gain of light sensor 402 such that the light sensor's response to the light signal can be within the operating range of the light sensor.

In some examples, device 400 can further include one or more light emitters or emitters 408 that can be activated in low-light conditions. If the detected light signals are too low (e.g., the DC level of light intensity is within a predetermined margin of the noise floor or falls below the noise floor), the controller can increase the gain of light sensor 402 such that the light sensor response to the light signal is within the operating range of the light sensor.

In some examples, ambient light levels may not be suitable (e.g., the signal-to-noise ratio is at or below a predetermined criteria such as a predetermined threshold value) for acquisition of physiologically relevant optical data. Light emitters 408 can be activated when the ambient light levels are too low to obtain a precise physiological measurement or when the controller. In some examples, light emitters 408 may not be activated when the user activates a power saving (e.g., low power) mode of the device, even if the ambient light levels are too low. The activated light emitter 408 can supplement the ambient light. In some examples, light emitter 408 can be configured to emit light at only one intensity level. In some examples, light emitter 408 can be configured to emit light at various intensity levels or gradients. One or more characteristics (e.g., intensity, pulse frequency, wavelength, etc.) of the emitted light can be determined at least in part by light detected by light sensor 402. For example, the intensity of light emitted can be selected such that the light sensor light response is within a specific range, where the specified range can be between the noise floor and the saturation level of the light sensor. Tailoring the characteristics of the emitted light based on the properties of light detected from light sensor 402 can help conserve the power consumption of device 400 by providing light at a sufficient intensity for procuring a physiologically relevant optical signal with a desired level of precision and/or signal-to-noise ratio. Emitting light that can be excessively bright (e.g., with a predetermined margin of the light sensor saturation level) can deplete the battery or power source.

In low lighting conditions, ambient light levels may be at or near the noise floor regardless of how high the gain is. In response, the controller can activate a light emitter (depending on the mode of operation or as desired by the user). The intensity of the light emitter can be sufficient to increase the light detected by the light sensor to within the operating range. For example, the darker the detected ambient light level, the greater the intensity of the activated light emitter. While some light emitters can be configured to output light at various intensities, other light emitter may only output light at one intensity.

In some examples, the device can include one or more modes that can be selected by the user or can be automatically triggered with certain lighting conditions or power consumption conditions (e.g., that can prioritize power consumption over measurement accuracy or vice versa). For example, the device can include a power-saving (e.g., low power) mode that can be selected by the user (e.g., to extend the length of time between charges) or can be selected by the controller when the battery level of the device meets or drops below a certain threshold level (e.g., when the remaining battery lower is less than 50% of its full capacity).

In some examples, device 400 can include a plurality of light sensors, as illustrated in FIG. 4B. Device 400 can include light sensor 412, light sensor 414, and controller 416. Controller 416 can be in communication with light sensor 412 via communication channel 418 and with light sensor 414 via communication channel 420. Light sensor 412 can be positioned to receive ambient light 406, while light sensor 414 can be position to receive light that has interacted with the body (e.g., skin) of the user. Light sensor 412 and/or light sensor 414 can have adjustable gain. For example, the gain of light sensor 414 can be adjusted according to levels of ambient light detected by light sensor 412. In some examples, device 400 can include a light emitter 411 to supplement ambient light in low-light conditions (and/or when controller 416 or the user activates a power-saving mode of the device). Supplementing ambient light can help boost the intensity of light detected by light sensor 414.

In some instances, the controller can activate light emitter 411 when one or more properties (e.g., associated with the physiological signals) of light detected by light sensor 414 (e.g., a physiological data sensor) is not within a predetermined range. For example, the shape of the physiological signal measured over a time interval may be indicative of low signal quality. In some examples, the signal-to-noise ratio (e.g., the intensity of the heart rate signal to the intensity of the motion noise) can be indicative of low signal quality. Light emitter 411 can be activated to help boost the quality of the physiological signal(s).

Figure 4C:
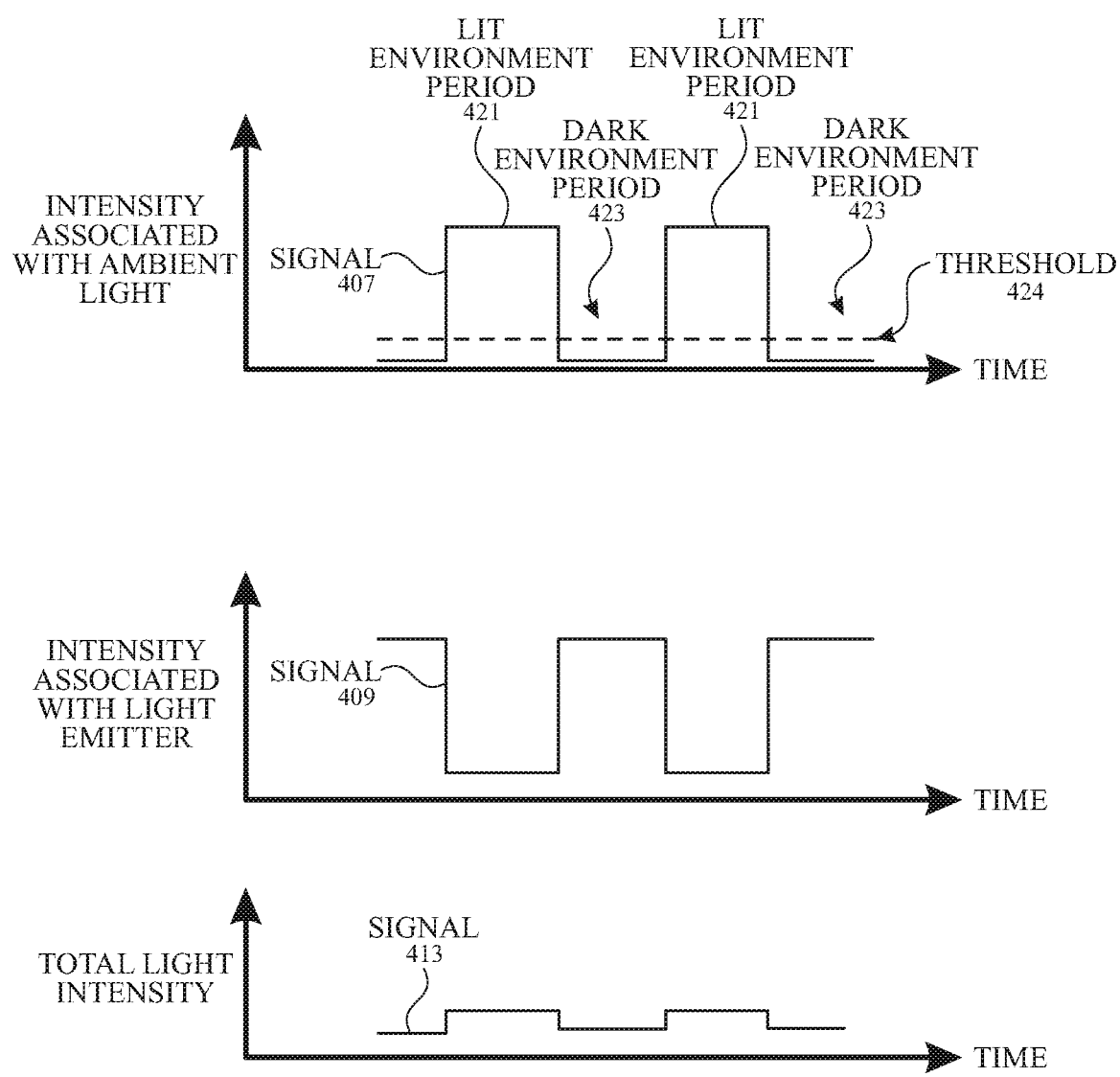
FIG. 4C illustrates exemplary timing diagrams of ambient light with large variations, the intensity of a light emitter, and the total intensity of light that has interacted with the user's skin according to examples of the disclosure.
Figure 4D:
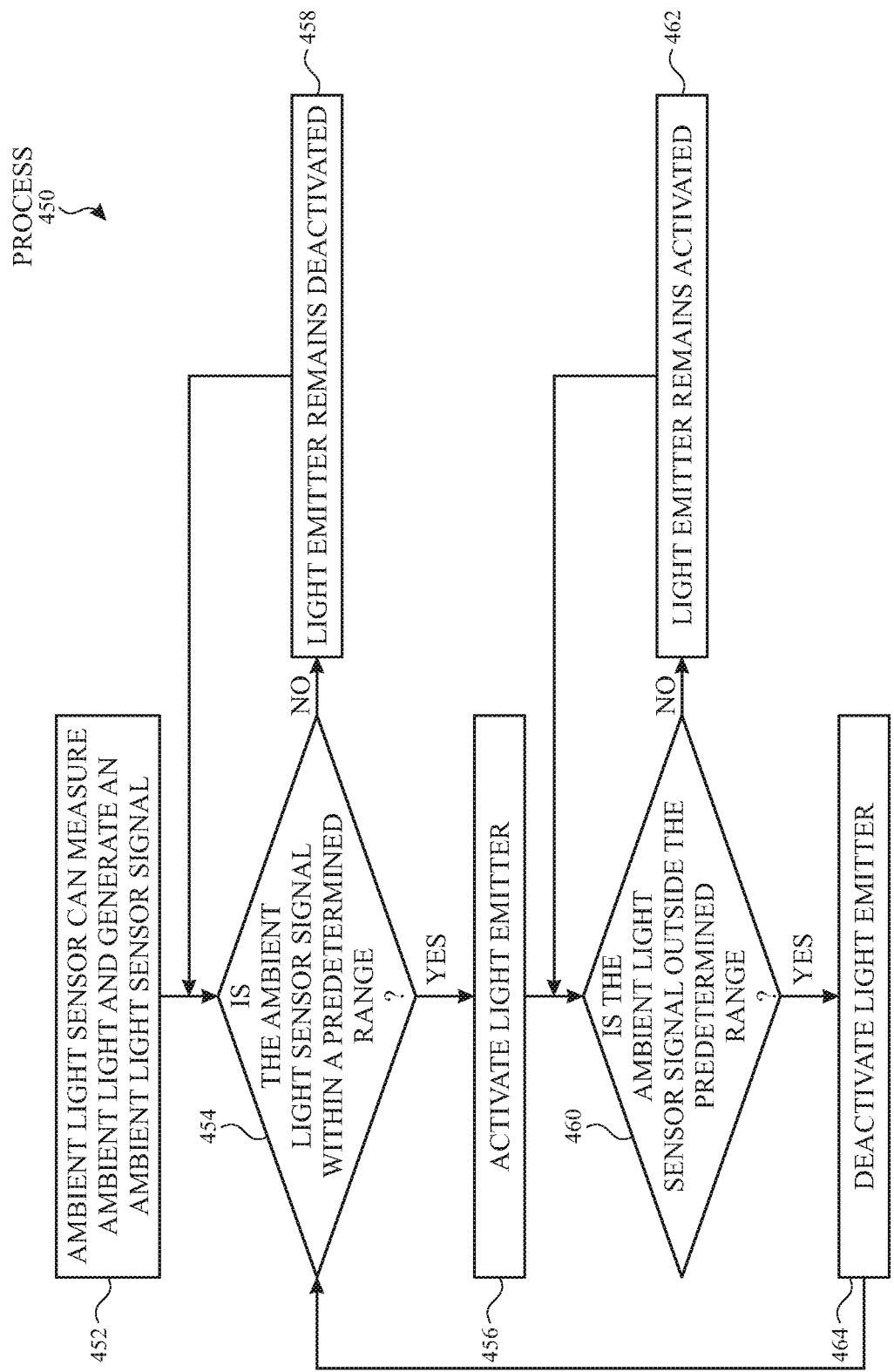
FIG. 4D illustrates an exemplary method for activating a light emitter in response to ambient light having large variations according to examples of the disclosure.

Additionally or alternatively, the sensed ambient light can include large (e.g., greater than physiological changes could yield) variations in amplitude, as illustrated in FIG. 4C. The device can execute an exemplary method for activating light emitter 411 based on the characteristics of the ambient light during a given time period, such as the process 450 illustrated in FIG. 4D. For example, the ambient light sensor can measure periods of dark light (i.e., dark environment periods 423) interspersed with periods of bright light (i.e., lit environment periods 421) (step 452 of process 450). Signal 407 can be a signal generated by light sensor 412 in response to detected ambient light 406. Signal 407 can include intensities greater than threshold 424 during lit environment periods 421 and intensities less than threshold 424 during dark environment periods 423.

The controller can determine whether the ambient light sensor signal is within a predetermined range (e.g., range indicative of a lit environment period 421) (step 454 of process 450). If the ambient light sensor signal is within a predetermined range (e.g., during a lit environment period 421), light emitter 411 can remain deactivated (step 458 of process 450). Otherwise, the controller can activate light emitter 411 in response to the large variations (step 456 of process 450). If the ambient light sensor signal falls outside the predetermined range (step 460 of process 450), the light emitter can be deactivated (step 464 of process 450). Otherwise, the light emitter can remain activated (step 462 of process 450). In some examples, the controller can activate light emitter 411 only during dark (e.g., not meeting a predetermined criteria such as being lower than a predetermined threshold) periods 423, as illustrated with signal 409.

By activating the light emitter 411 during only dark environment periods 423, the differences in total light intensity (i.e., intensity of ambient light 406 and light emitted by light emitter 411) can be minimized or reduced, as illustrated with signal 413, and light interacting with the user can include less variability. With less variability, the controller can configure the light sensor(s) to have a constant gain.

Although FIG. 4C illustrates signal 407 as being associated with the intensity of ambient light, examples of the disclosure can include adjusting the intensity of the light emitter based on signals from an accelerometer in addition to, or instead of, the signals from the ambient light sensor. For example, a user can be walking with his or her hand swinging back and forth. The back and forth hand motion can be associated with large variations in the accelerometer signal, large variations in the ambient light signal (e.g., light sensor 412 being exposed followed by being unexposed to ambient light 406), or both. The back and forth hand motion can be associated with the user's cadence (e.g., running or other periodic activity with 50 bpm). The accelerometer signal can include information associated with acceleration. Information associated with acceleration can include, but is not limited to, acceleration intensity and an acceleration profile (e.g., a pattern of acceleration over a given time frame).

Examples of the disclosure can include adjusting the intensity of the light emitter based on user input (e.g., light emitter activation can be triggered when the user chooses an activity on the touch screen). In some examples, the controller can exclude the signals (e.g., physiological signals) from light sensor 414 measured during dark environment periods 423 from the determination of the user's physiological information.

Although the discussion above and associated drawings may refer to light sensors as, for example, two light sensors, examples of the disclosure can include a single light sensor that can function as both an ambient light sensor and a physiological data light sensor. For example, the light sensor can be positioned and configured to detect ambient light and physiologically relevant light (i.e., light that has interacted with the user's body) at various or sequential time intervals.

Figure 5A:
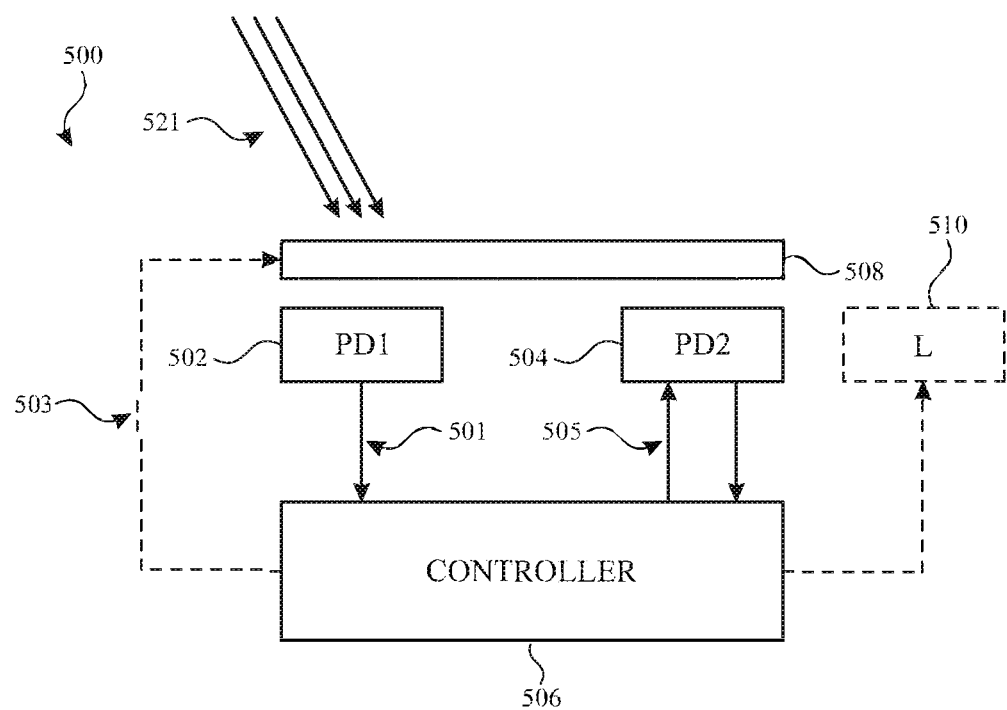
FIG. 5A illustrates an exemplary block diagram of a device including a variable opacity element according to examples of the disclosure.

In some examples, the intensity of light received by the light detectors can be adjusted using one or more variable opacity elements (e.g., filters such as polarizing filters and wavelength specific filters). The variable opacity elements can be disposed over one or more light sensors. FIG. 5A illustrates an exemplary block diagram of a device including a variable opacity element according to examples of the disclosure. Device 500 can include light sensor 502, light sensor 504, controller 506, and light emitter 510. Controller 506 can be in communication with light sensor 502 and light sensor 504 via communication channel 50/ and communication channel 505, respectively. A variable opacity element 508 can be positioned in the input light path for light sensor 502 and light sensor 504. Light sensor 502 can be positioned to receive ambient light 521, while light sensor 504 can be positioned to receive light that has interacted with the body of the user. Although the figure illustrates variable opacity element 508 as modifying the input light for both light sensors (e.g., light sensor 502 and light sensor 504), examples of the disclosure can include the variable opacity element as modifying the input light for only light sensor 504 (i.e., the variable opacity element can be located in the input light path for the light sensor coupled to light interacting with the user).

In some examples, a variable opacity element can include a photochromic material (e.g., spiropyrans, spiroperimidines, diarylethenes, fulgides, hexaarylbiimidazole, or azonbenzenes). Accordingly, the opacity (e.g., transmission of light through) of the element may not be adjusted according to commands from controller 506. In some examples, variable opacity element 508 can include a controllable material, which can allow a certain percentage of transmission of light based on command from controller 506 via communications channel 503. Examples of the disclosure can further include liquid crystal material, "smart" glass (e.g., including polymer dispersed liquid crystals), and electronic micro-blinds as variable opacity elements. One or more of these materials can, additionally or alternatively, be used as an incident light angular acceptance element, as discussed below.

Figure 5B:
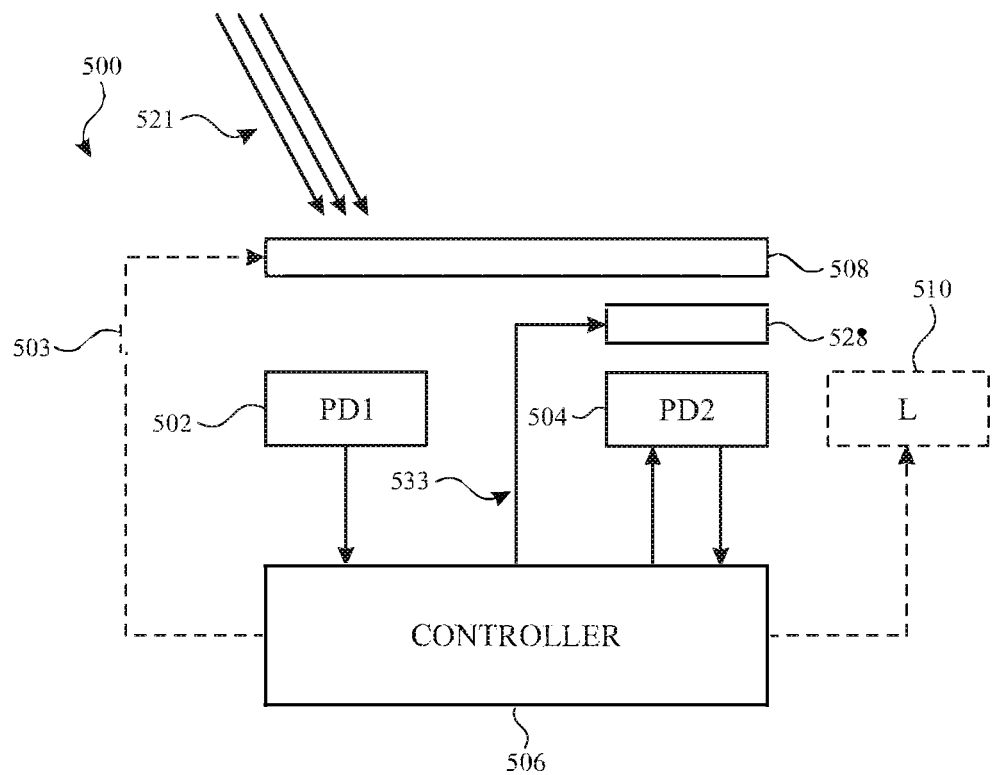
FIG. 5B illustrates an exemplary block diagram of a device including multiple variable opacity elements according to examples of the disclosure.

In some examples, the device can include multiple variable opacity elements. For example, each light sensor can be optically coupled to a different variable opacity element, where each variable opacity element can have the same or different optical properties. FIG. 5B illustrates an exemplary block diagram of a device including multiple variable opacity elements according to examples of the disclosure. Device 500 can include two variable opacity elements, such as variable opacity element 508 and variable opacity element 528. Variable opacity element 508 can be positioned in the input light path for light sensor 502 and light sensor 504. Variable opacity element 528 can be positioned in the input light path for light sensor 504. Controller 506 can communicate with variable opacity element 528 via communication channel 533. In some examples, the light sensor (e.g., light sensor 502) configured to receive ambient light 521 can be optically coupled to a fewer number (e.g., one) variable opacity elements than the light sensor (e.g., light sensor 504) configured to receive light that has interacted with the user.

In some examples, variable opacity element 528 can include a wavelength selective component (e.g., filter) that can transmit a selected one or more wavelengths of interest. For example, controller 506 can determine that a particular wavelength of light can include physiologically relevant optical information and can adjust variable opacity element 528 via communication channel 533 to allow a greater percentage of transmission of light having the particular wavelength. In some examples, controller can adjust variable opacity element 528 via communication channel 533 to prevent or reduce the transmission of light having other wavelengths. In some examples, the variable opacity element can include a neutral density filter.

In some instances, the controller can change one or more optical properties (e.g., opacity) of variable opacity element 508 when one or more properties (e.g., associated with the physiological signals) of light detected by light sensor 504 (e.g., a physiological data sensor) is not within a predetermined range. For example, the shape of the physiological signal measured over a time interval may be indicative of low signal quality. In some examples, the signal-to-noise ratio (e.g., the intensity of the heart rate signal to the intensity of the motion noise) can be indicative of low signal quality. The optical properties of variable opacity element 508 can change (e.g., the opacity can be reduced) to help boost the quality of the physiological signal(s).

Figure 5C:
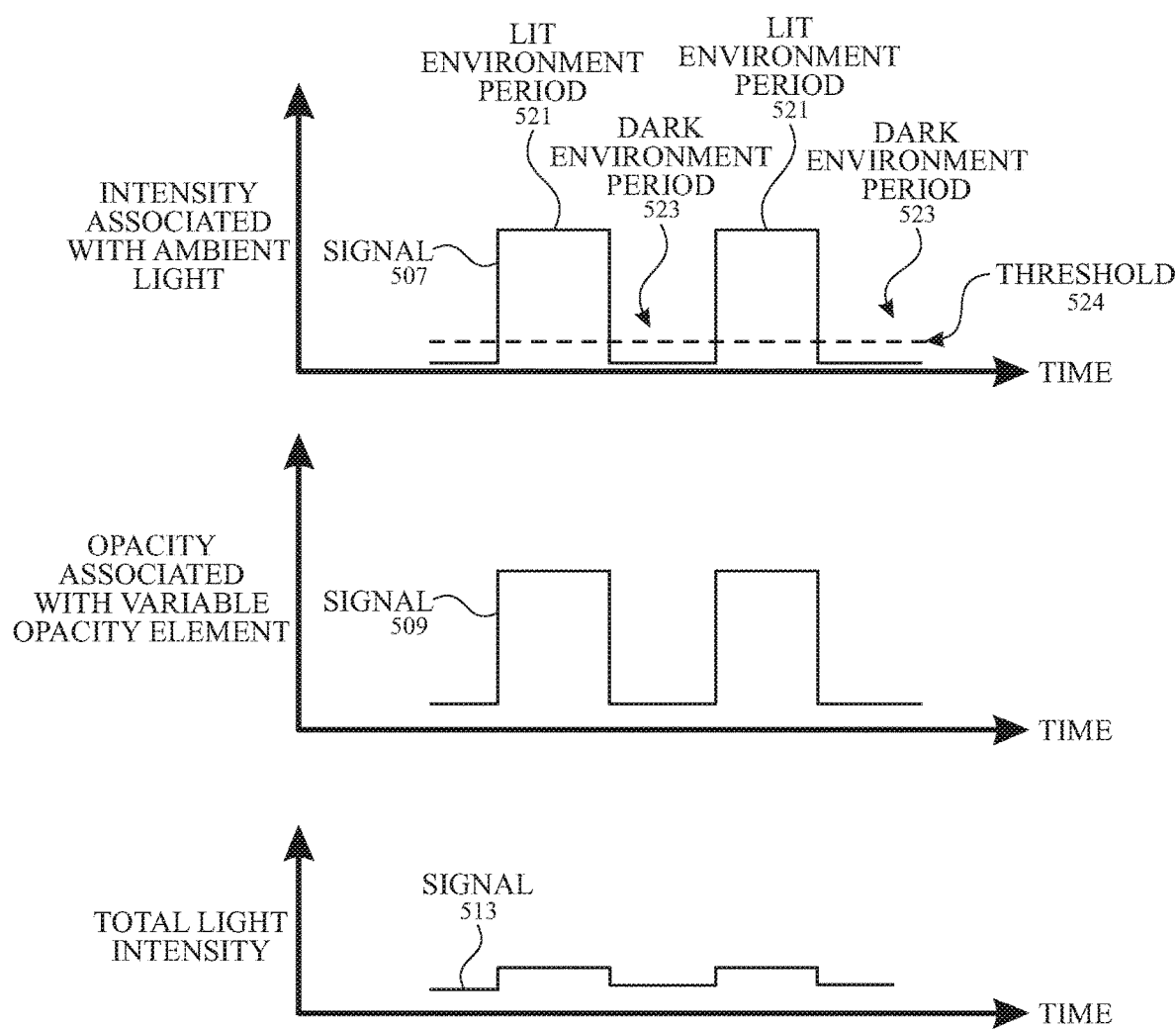
FIG. 5C illustrates exemplary timing diagrams of ambient light with large variations, the opacity of a variable opacity element, and the total intensity of light that has interacted with the user's skin according to examples of the disclosure.
Figure 5D:
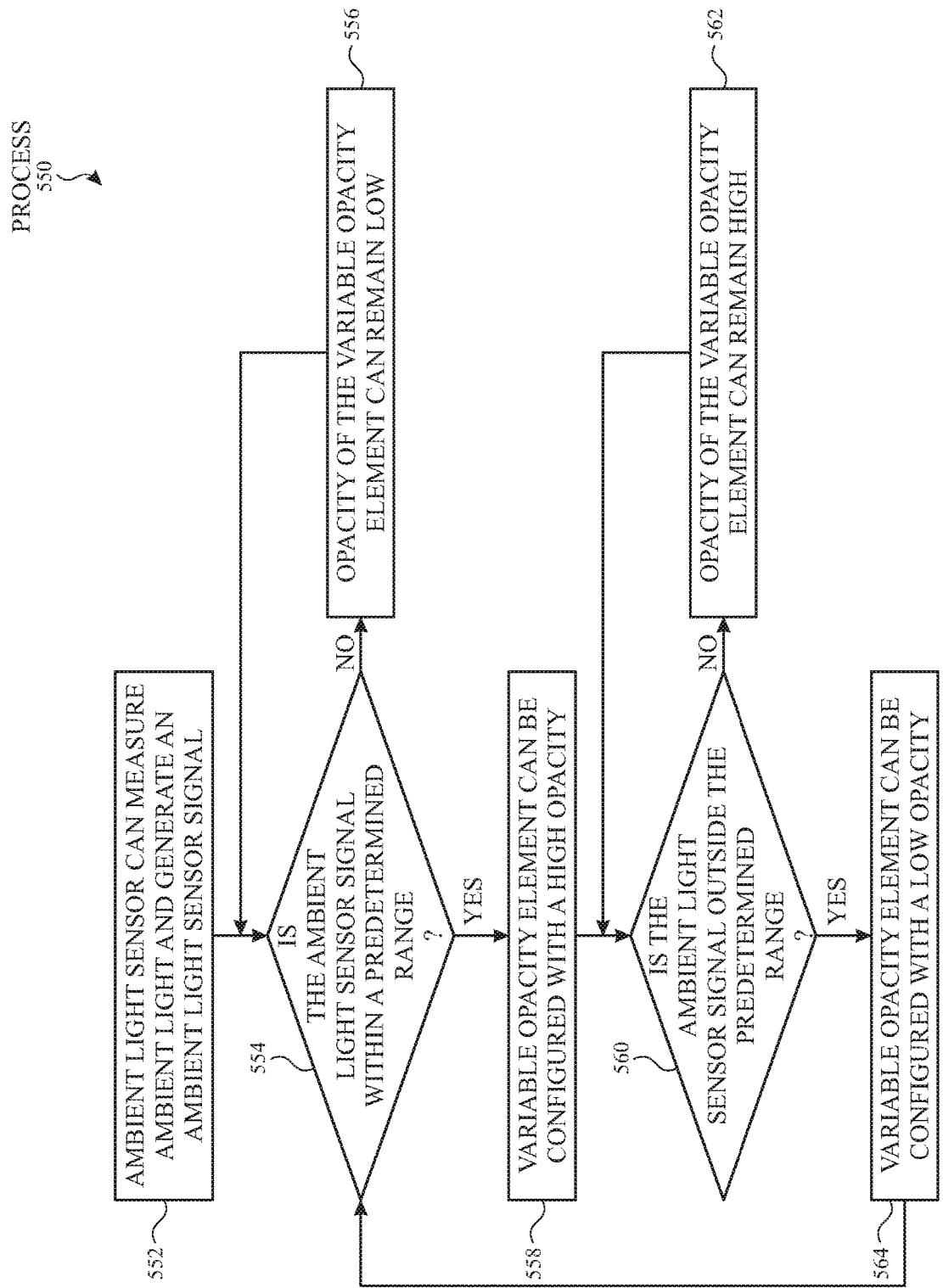
FIG. 5D illustrates an exemplary method for configuring the opacity of a variable opacity element in response to ambient light having large variations according to examples of the disclosure.

Additionally or alternatively, the ambient light signal can include large (e.g., greater than physiological changes could yield) variations in amplitude, as illustrated in FIG. 5C. The device can execute an exemplary method for varying the opacity of variable opacity element 508 based one or more characteristics of ambient light 521 during a given time period, such as the process 550 illustrated in FIG. 5D. For example, light sensor 502 (e.g., ambient light sensor) can measure periods of dark light (i.e., dark environment periods 523) interspersed with periods of bright light (i.e., lit environment periods 521) (step 552 of process 550). Signal 507 can be a signal generated by light sensor 512 in response to detected ambient light 506. Signal 507 can include intensities greater than threshold 524 during lit environment periods 521 and intensities less than threshold 524 during dark environments 523.

Variable opacity element 508 can begin with a low opacity (e.g., 80-90% transmittance). The controller can determine whether the ambient light sensor signal is within a predetermined range (e.g., range indicative of a lit environment period 521) (step 554 of process 550). If the ambient light is not within a predetermined range (e.g., ambient light sensor signal indicates a dark environment period 523), the opacity of variable opacity element 508 can remain low (step 556 of process 550). Alternatively, variable opacity element 508 can begin with a high opacity (e.g., 10-20% transmittance) and can switch to low opacity when the controller determines the ambient light is not within the predetermined range. If the ambient light sensor signal is within a predetermined range (e.g., ambient light sensor signal indicates a lit environment period 521), variable opacity element 508 can be configured with a high opacity (step 558 of process 550). If the ambient light sensor signal falls outside the predetermined range (step 560 of process 550), variable opacity element 508 can be configured with a low opacity (step 564 of process 550). Otherwise, the opacity of variable opacity element 508 can remain high (step 562 of process 550). In this manner, the controller can synchronize the opacity of variable opacity element 508 to coincide with certain periods of the ambient light levels, as illustrated with signal 509.

By configuring variable opacity element 508 to have low opacity during only dark environment periods 523 and/or high opacity during only lit environment periods 521, the differences in total light intensity (i.e., intensity of ambient light 521 that interacts with the user during both lit environment periods 521 and dark environment periods 523) can be minimized or reduced, as illustrated with signal 513, and light interacting with the user can include less variability. With less variability, the controller can configure the light sensor(s) to have a constant gain.

Although FIG. 5C illustrates signal 507 as being associated with the intensity of ambient light, examples of the disclosure can include adjusting the opacity of the variable opacity element based on signals from an accelerometer in addition to, or instead of, the signals from the ambient light sensor. For example, a user can be walking with his or her hand swinging back and forth. The back and forth hand motion can be associated with large variations in the accelerometer signal, large variations in the ambient light signal (e.g., light sensor 502 being exposed followed by being unexposed to ambient light 521), or both. The back and forth hand motion can be associated with the user's cadence (e.g., running or other periodic activity with 50 bpm). Examples of the disclosure can include adjusting the intensity of the light emitter based on user input (e.g., light emitter activation can be triggered when the user chooses an activity on the touch screen). In some examples, the controller can exclude the signals (e.g., physiological signals) from light sensor 502 and/or light sensor 504 measured during dark environment periods 523 from the determination of the user's physiological information.

Figure 6A:
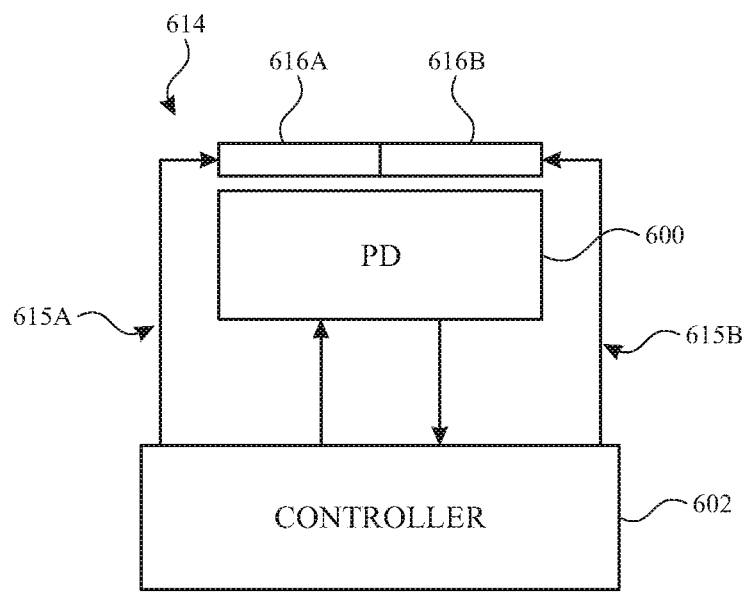
FIG. 6A illustrates an exemplary block diagram of a device including a variable opacity element including multiple sections according to examples of the disclosure.

In some examples, the variable opacity element can include multiple sections, where each section can affect the transmission of various wavelengths of light different. FIG. 6A illustrates an exemplary block diagram of a device including a variable opacity element including multiple sections according to examples of the disclosure. Variable opacity element 614 can include a first portion 616*a* and a second portion 616*b*. First portion 616*a* can affect the transmission of light according to commands from controller 602 via communications channel 615*a*. Second portion 616*b* can affect the transmission of light according to commands from controller 602 via communications channel 615*b*. In some examples, light sensor 600 can be a pixel-based light sensor, where certain regions of the light sensor can correspond/map to the first portion 616*a* and certain other regions of the light sensor can correspond/map to the second portion 616*b*. For example, if controller determines (e.g., based on levels of ambient light detected by another light sensor) that the ambient light includes a high (e.g., greater than 50%) proportion of ultraviolet light compared to green light (or any other wavelengths that may, for example, include physiologically relevant information), the opacity at region 616*a* for ultraviolet light can be increased, and the opacity at region 616b for green light can be decreased. Tailoring different sections of variable opacity element 614 can help reduce the likelihood of saturating light sensor 600 with light that can include little or no data relevant to physiological information. Excluding data that has little or no relevance to physiological information can facilitate with the accuracy in the measurement and determination of the user's physiological information.

Figure 6B:
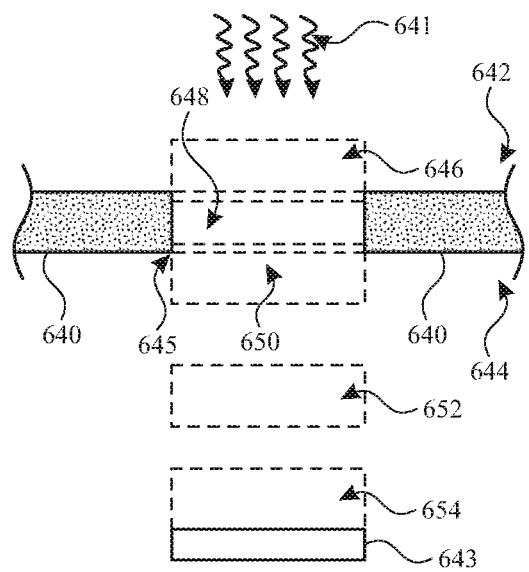
FIG. 6B illustrates a schematic representation of exemplary locations of a variable opacity element according to examples of the disclosure.

The variable opacity elements can be located at a point along the input path to a light sensor. FIG. 6B illustrates a schematic representation of exemplary locations of a variable opacity element according to examples of the disclosure. Housing 640 of a device can have an exterior surface 642, an interior surface 644, and light transmitting region (e.g., opening 645). Interior surface 644 can be located closer to internal components (e.g., light sensor 643) of the device than exterior surface 642. Light 621 can transmit through opening 645 to light sensor 643. Light 641 can include ambient light and/or light that has interacted with the body of the user. The variable opacity element can be located at or along the exterior of housing 640 at location 646. In some examples, the variable opacity element can be located within the thickness of housing 640. For example, the variable opacity element can be flush with the exterior surface of housing 640 at location 648. In some examples, the variable opacity element can be located at or along the interior surface of housing 640 at location 650. In some examples, variable opacity element can be located entirely within housing 650. For example, the variable opacity element can be located between interior surface 644 and light sensor 643 at location 652. Alternatively, variable opacity element can be in direct contact with, or deposited on, light sensor 643 at location 654.

Figure 7A:
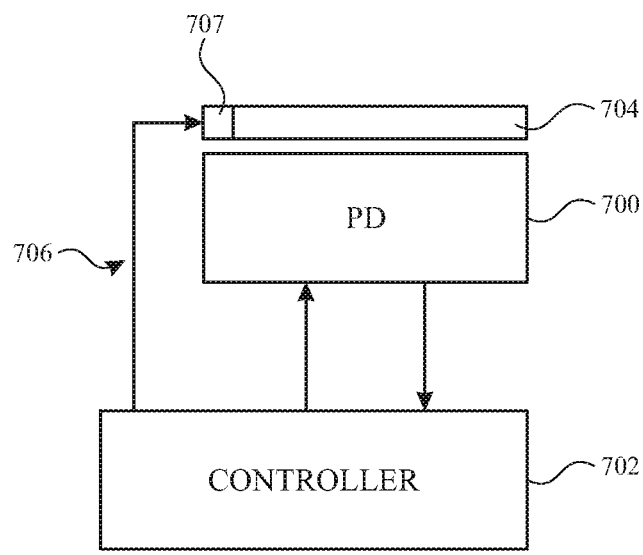
FIGS. 7A-7B illustrate schematic representations of a movable variable opacity element according to examples of the disclosure.
Figure 7B:
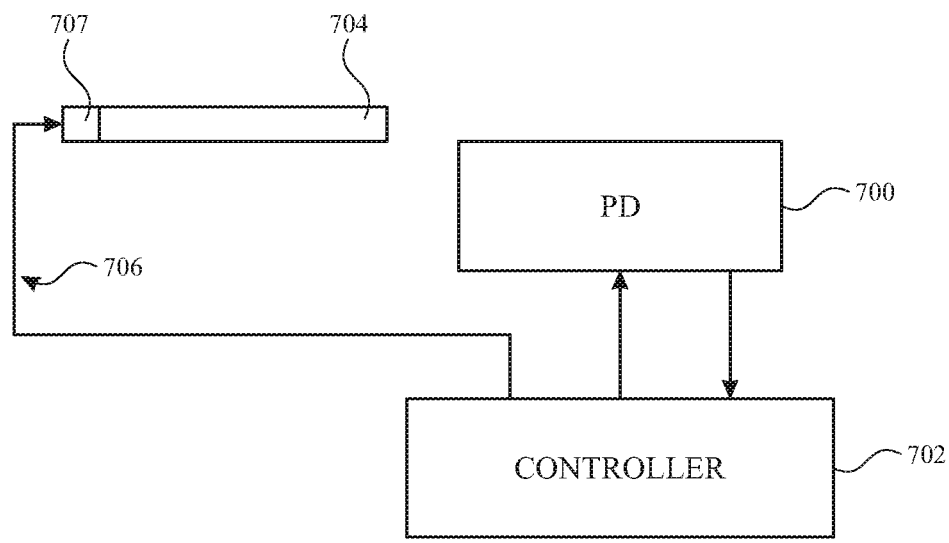

In some examples, the device can include a variable opacity element that can be configured to move into and out of the light path of the light sensor. FIGS. 7A-7B illustrate schematic representations of a movable variable opacity element according to examples of the disclosure. The device can include light sensor 700, variable opacity element 704, and controller 702. Controller 702 can be in communication with light sensor 700 and, in some examples, can be in communication with variable opacity element 704. For example, controller 702 can send one or more signals to variable opacity element 704 when the variable opacity element includes a controllable material. Alternatively, controller 702 may not send signals to variable opacity element 704 when the variable opacity element is a filter or photochromic material.

Although not illustrated in the figures, examples of the disclosure can include the device having additional components such as a second light sensor and/or a light emitter. In some examples, the device can further include a motion system 707 that can be coupled to variable opacity element 704. Motion system 707 can be, for example, a motor or an actuator. Motion system 707 can be in communication with controller 702 via communication channel 706 to control the position (i.e., motion state) of variable opacity element 704.

As illustrated in FIG. 7A, motion system 707 can cause variable opacity element 704 to be located in a first position. The first position can cause variable opacity element 704 to be located in the light path of light sensor 700. Motion system 707 can change the position of variable opacity element 704 to a second position, as illustrated in FIG. 7B. The second position can cause variable opacity element 704 to be located outside of the light path of light sensor 700. In some examples, the location or position of variable opacity element 704 can be determined at least in part by levels of light detected by light sensor 700 or another light sensor.

For example, if ambient light levels meet or exceed a predetermined criteria (e.g., a light intensity greater than a predetermined brightness value), motion system 707 can move variable opacity element 704 such that variable opacity element 704 can be located in the light path of light sensor 700. In this manner, the intensity of incoming light to light sensor 700 can be reduced, thereby reducing the likelihood of saturating light sensor 700. As another example, if ambient light levels do not meet a predetermined criteria (e.g., the light intensity is less than a predetermined threshold), motion system 707 can move variable opacity element 704 out of the light path of light sensor 700. The intensity of incoming light to light sensor 700 may not be reduced, and suitable signal levels can be used for accurate measurements.

Figure 8A:
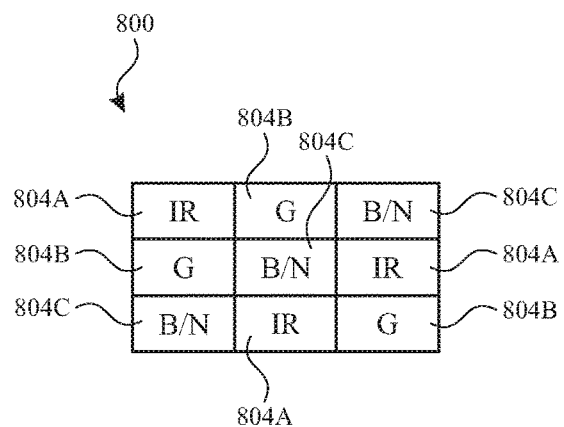
FIGS. 8A-8B illustrate top views of exemplary filter arrays according to examples of the disclosure.
Figure 8B:
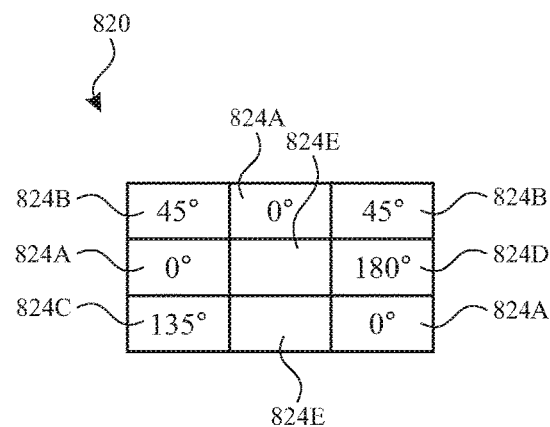
Figure 8C:
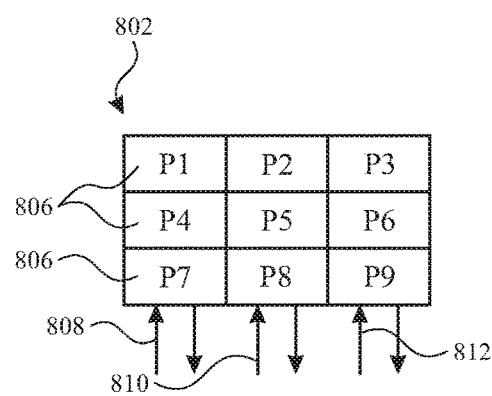
FIG. 8C illustrates a top view of an associated light sensor according to examples of the disclosure.

Alternatively or additionally, the device can include one or more light sensors along with one or more filters disposed over the one or more light sensors. FIGS. 8A-8C illustrate an exemplary filter array and associated light sensor according to examples of the disclosure. The filter array can include a plurality of filter units 804 for multiple different optical characteristics. These optical characteristics can include, but are not limited to, wavelengths of light and angles of light incidence.

For example, as illustrated in FIG. 8A, the filter array 800 can be a color filter array including filters for different wavelength ranges. The filter array 800 can include one or more filter units 804A for a first wavelength range (e.g., three infrared filter units), one or more filter units 804B for a second wavelength range (e.g., three green filter units), and one or more filter units 804C for a third wavelength range (e.g., three blue filter units), where the wavelength ranges can be different from each other.

Although the figure illustrates a certain pattern of how the filter units 804A-C of one type can be arranged relative to the filter units 804A-C of the other types, examples of the disclosure can include any pattern (e.g., an interleaved pattern where filters on one type alternate with filters of another type). In some examples, the color filter array 800 can be a single layer. Additionally, examples of the disclosure are not limited to infrared, green, and blue color filters, but can include color filters of any wavelength range.

As another example, as illustrated in FIG. 8B, the filter array 820 can be a directional filter array including filters for different angles of incidence. The filter array 800 can include one or more filter units 824A for a first angle of incidence (e.g., 0°), one or more filter units 824B for a second angle of incidence (e.g., 45°), one or more filter units 824C for a third angle of incidence (e.g., 135°), and one or more filter units 824D for a fourth angle of incidence (e.g., 180°). As another example, one filter unit 824A can be configured with a 0° directional bias, another filter unit 824A can be configured with a 270° directional bias, and another filter unit 824A can be configured with a 315° directional bias. One filter unit 824B can be configured with a 45° directional bias, and another filter unit 824B can be configured with a 225° directional bias. The filter unit 824C can be configured with a 135° directional bias, and the filter unit 824D can be configured with a 180° bias. In some examples, the filter array 820 can include one or more units 824E that may not include a directional bias. For example, the units 824E can include a transparent material (e.g., a window) and can be used for obtaining a baseline measurement for subsequent comparison to information measured by the other units

824A-E. For example, one unit 824E can be a filter unit configured with a 90° directional bias.

Although the figure illustrates a certain pattern of how the filter units 824A-E of one type are arranged relative to the filter units 824A-E of the other types, examples of the disclosure can include any pattern (e.g., an interleaved patterned). The directional filter array can be a single layer (e.g., the angular acceptance element can be integrated with the variable opacity element) or can include multiple layers (e.g., the angular acceptance element can be located on a separate and different layer than the variable opacity element). For example, one layer can include a liquid crystal material or another electrically controlled material. Another layer can include a passive, segmented directional filter. Additionally, examples of the disclosure are not limited to 0°, 45°, 135°, and 180° filters, but can include direction filters of any angle of incidence. Additionally, one or more direction filter units 824A-E can be configured to accept a range of acceptance angles (e.g., 0°-10°).

The filter array 800 can be disposed over a light sensor 802, as shown in FIG. 8C. The light sensor 802 can have the same number of detector units (e.g., pixels Pl-P9) 806 as the number of filter units (e.g., color filter units 804A-C or directional filter units 824A-E). In some examples, each filter unit can map to a single detector pixel 806. In some examples, a single filter unit can map to a plurality of detector pixels or regions on the detector surface. With mapping of the detector pixels to the filters units, channels having specific optical characteristics (e.g., wavelength-specific or incident-angle specific) can be formed. For example, detector pixels 806 that map to an infrared color filter unit 804A can form an infrared channel. The controller can read out from and adjust the gain of the detector pixels 806 in the infrared channel via communications connection 808. Similarly, detector pixels 806 that map to a green color filter unit 804B can form a green channel, and detector pixels 806 that map to a blue color filter unit 804C can form a blue channel. The controller can read out from and adjust the gain of the detector pixels 806 in the green channel via communications connections 810. The controller can also read out from and adjust the gain of the detector pixels 806 in the blue channel via communications channel 812.

As another example, detector pixels that map to a 45° directional filter unit 824B can form a 45° channel. The controller can read out from and adjust the gain of the detector pixels 806 in the 45° channel via communications connection 808. Similarly, detector pixels 806 that map to a 0° filter unit 824A can form a 0° channel. Detector pixels 806 that map to a 135° filter unit 824C can form a 135° channel, and detector pixels 806 that map to a 180° filter unit 824D can form a 180° channel. The controller can read out from one or more communication connections (e.g., communication connections 810 and/or communication channels 812) and can adjust the gain of the detector pixels 806 in the respective channel via the communications connections.

In some examples, the gain of detector pixels 806 in a given channel can be independently adjusted from the gain of detector pixels 806 in other channels. Independent adjustment of wavelength-specific channels can help facilitate acquisition of light information having one or more physiologically relevant information, while reducing the inclusion of light information having physiologically irrelevant information (e.g., data).

Exemplary filters can include a color filter array, a directional filter array, and a mosaic filter (e.g., a Bayer filter). In some examples, the filter can include a plurality of filter units arranged in a matrix having a size that can correspond to the size of the light detection area of the light sensor. Each filter unit can transmit one or more wavelengths while blocking other wavelengths. In some examples, filter units can be repeatedly tiled across the filter array. In some examples, every filter unit can be unique or different from every other filter unit. Each filter unit can correspond to a particular detector pixel and/or detector region of the light sensor. The filter unit-detector pixel mapping can be predetermined and stored in memory.

In some examples, the gain of each filter unit and/or the group of filter units (e.g., of the same wavelength) can be adjusted by the controller in accordance with the ambient light levels. For example, a first light sensor (which may or may not have a color filter array) can be positioned to detect ambient light. The levels of detected ambient light can be used to adjust the gain of a second light sensor and/or control the opacity of the filter units in a color filter array disposed over the second light sensor. The gain of the pixels of the second light sensor can be individually controllable or may be grouped together. The grouping can be based on, for example, wavelength, where the gain of the group of pixels can correspond to a particular one or more wavelengths that can be adjust together to have the same gain. Wavelength-specific gain control can allow the device to select light including certain data of interest (e.g., physiologically relevant data) for post-processing and/or computation of the user's physiological information (e.g., heart rate or breathing rate), while ignoring (e.g., reducing the sampling and/or storage of) detected light that may include less useful information (e.g., noise). In this manner, accuracy and precision of the computation and determination of the physiological information can be enhanced.

Although the figure illustrates nine filter units, examples of the disclosure can include any number of filter units (e.g., 4, 12, 16, 26, etc.). Additionally, the filter units can be arranged in any configuration (e.g., alternating rows of one type of filter unit).

Figure 9A:
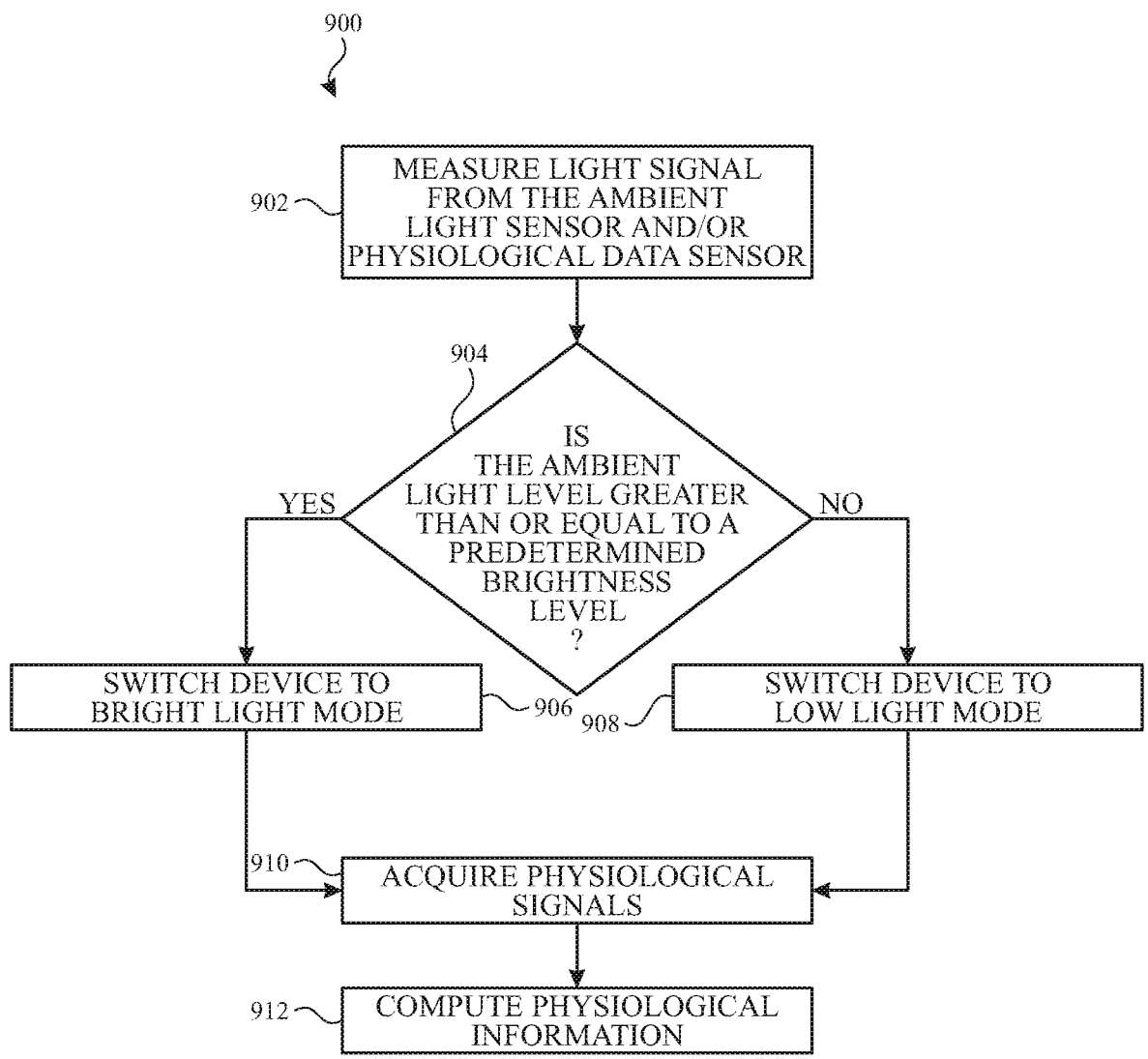
FIG. 9A illustrates an exemplary method for adjusting the gain based on ambient light levels according to examples of the disclosure.

In some examples, the controller can adjust the gain of a light sensor based on the light conditions detected by an ambient light sensor. FIG. 9A illustrates an exemplary method for adjusting the gain based on ambient light levels according to examples of the disclosure. Method 900 can include determining or checking/measuring ambient light levels (step 902 of process 900). The ambient light can be measured using an ambient light sensor and/or a physiological data light sensor. The controller can compare the ambient light levels to predetermine threshold value(s) (e.g., predetermined brightness level) (step 904 of process 900). If the ambient light levels meet a predetermined criteria (e.g., the ambient light levels are greater than or equal to the predetermined threshold value(s)), then the device can switch to a bright light mode (step 906 of process 900). Otherwise, the device can switch to a low light mode (step 908 of process 900).

Figure 9B:
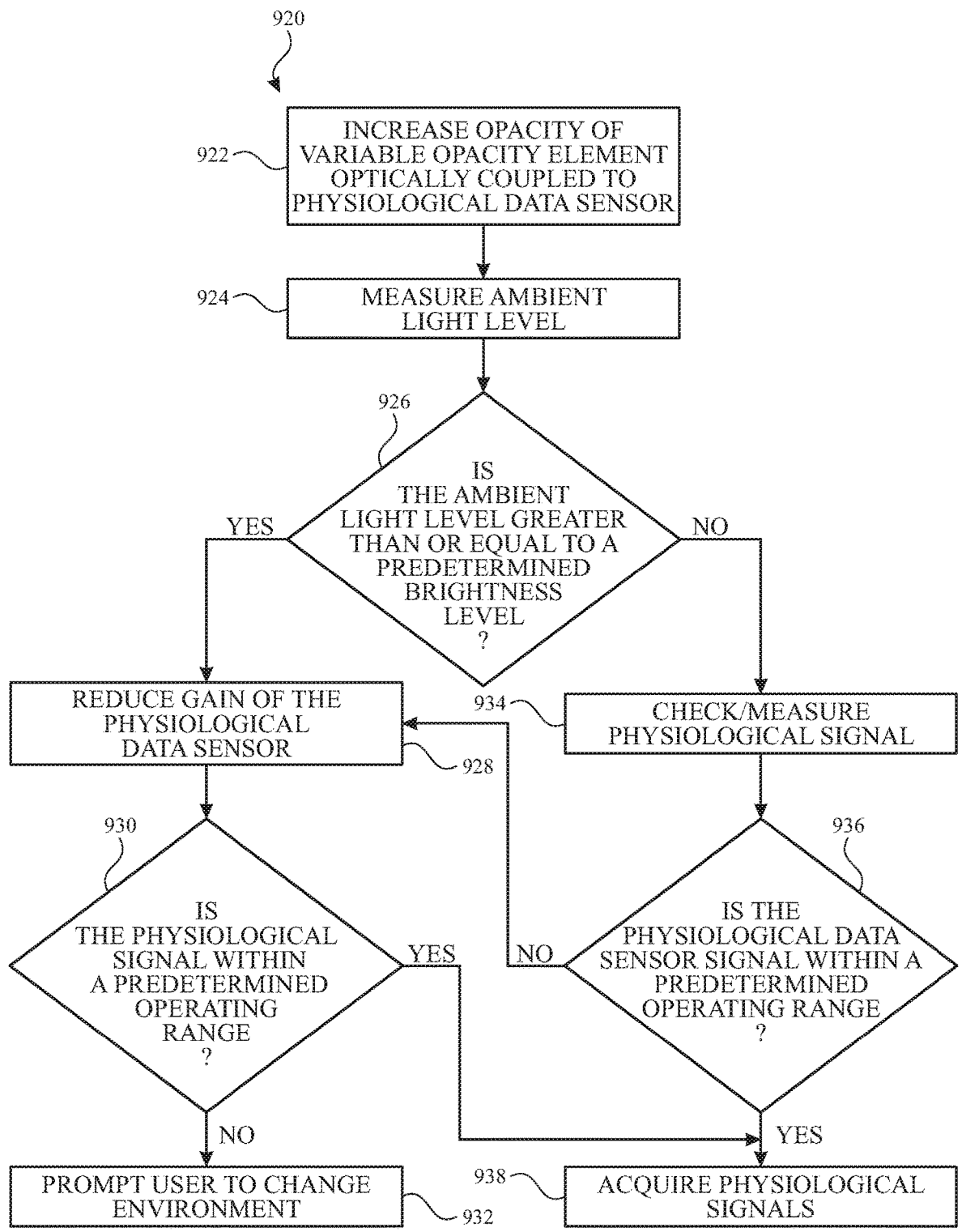
FIG. 9B illustrates an exemplary method for switching the device to a bright light mode according to examples of the disclosure.
Figure 9C:
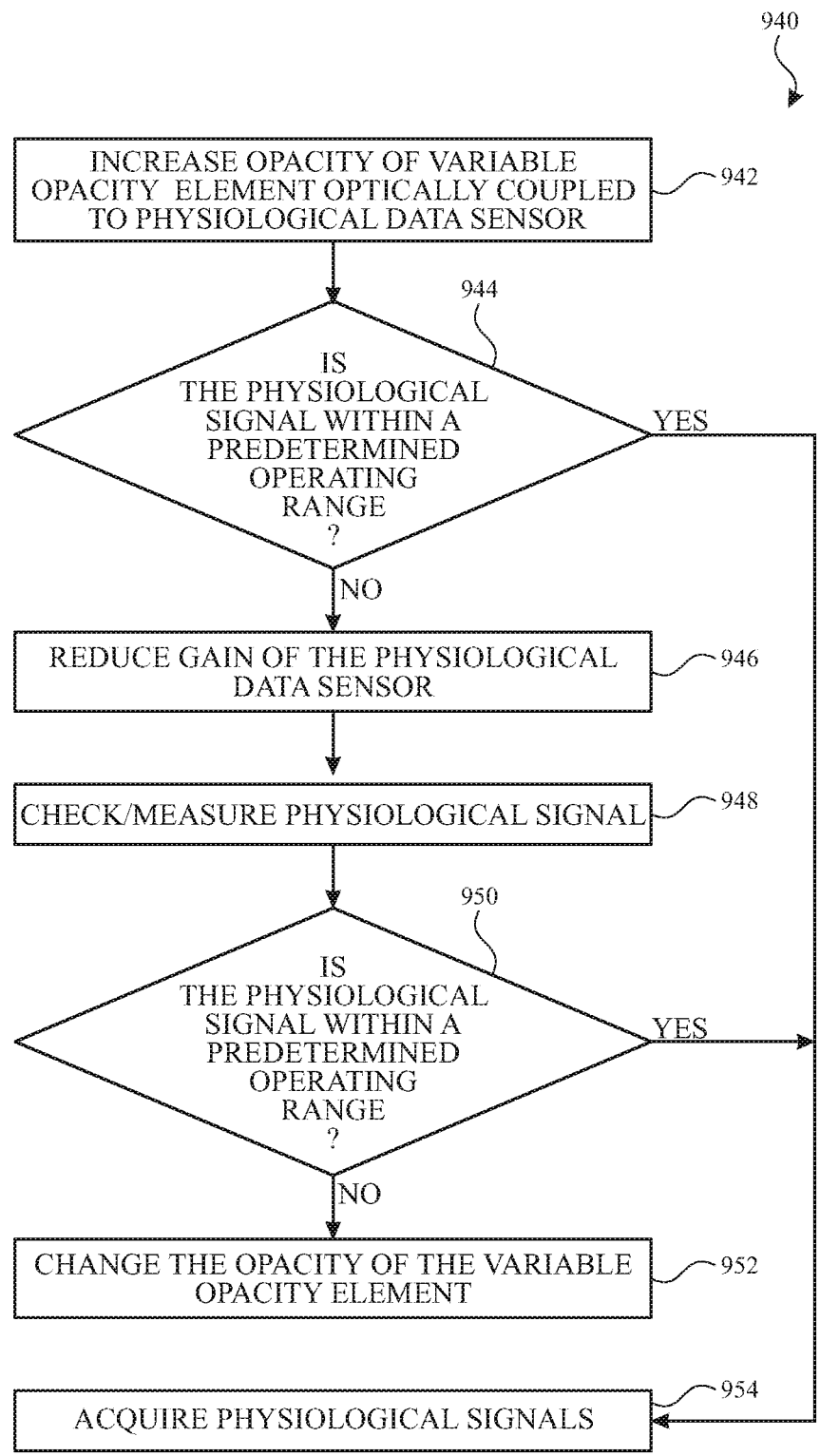
FIG. 9C illustrates an exemplary method for switching the device without a variable opacity element optically coupled to the ambient light sensor to a bright light mode according to examples of the disclosure.
Figure 9D:
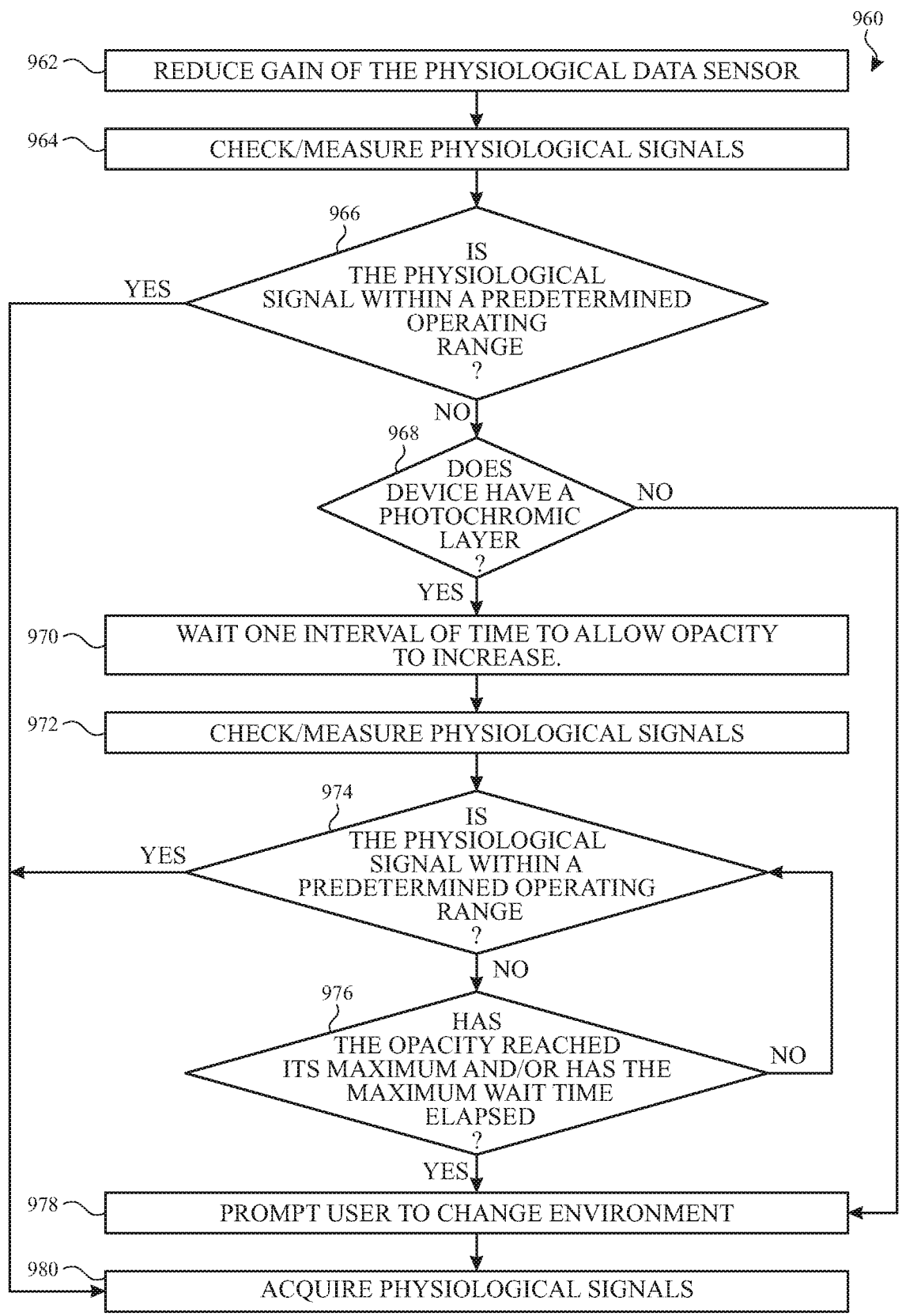
FIG. 9D illustrates an exemplary method for switching the device without a variable opacity element to a bright light mode according to examples of the disclosure.
Figure 9E:
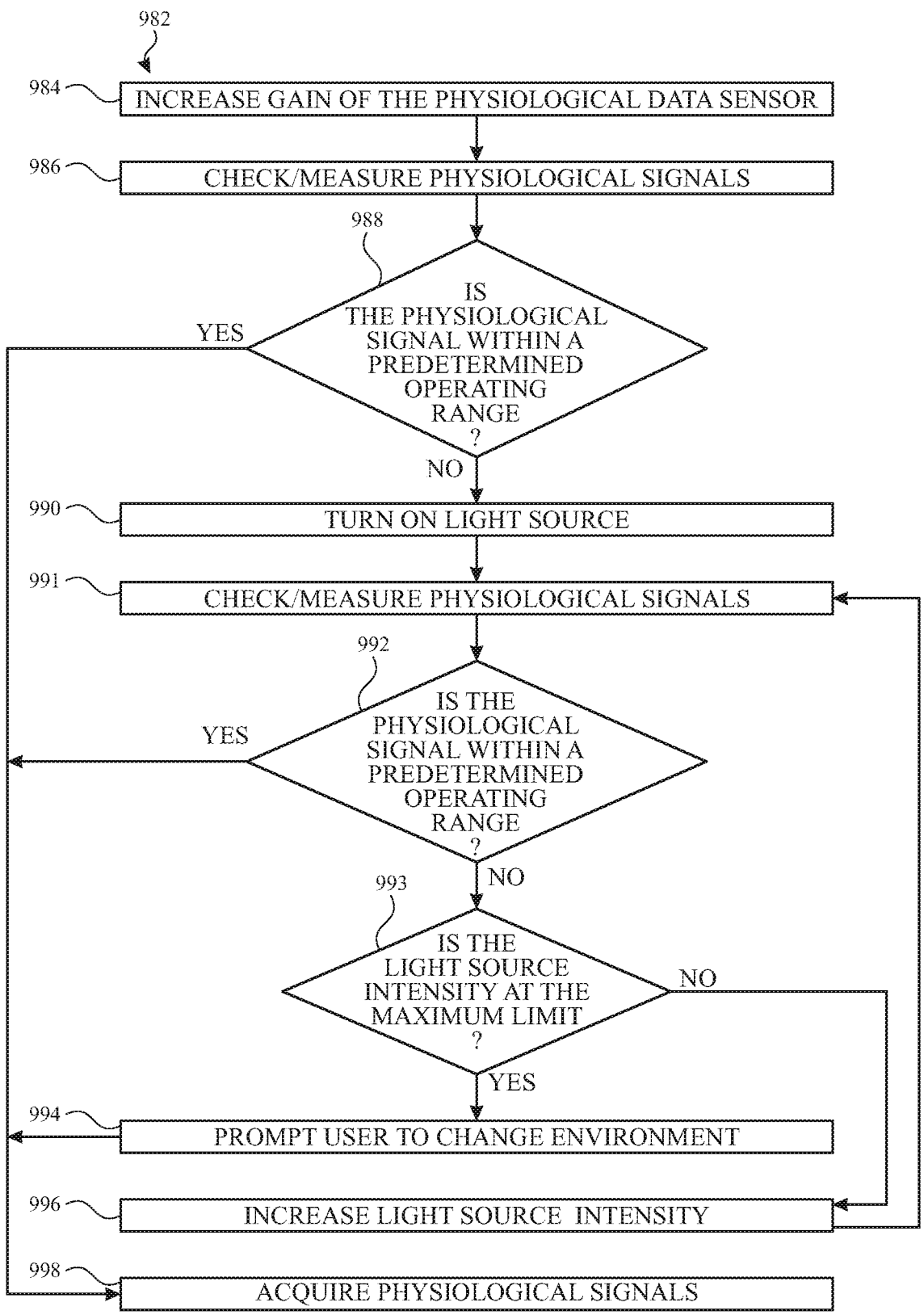
FIG. 9E illustrates an exemplary method for switching the device to a low light mode according to examples of the disclosure.

Switching to the bright light mode, as illustrated in FIGS. 9B-9D, or low light mode, as illustrated in FIG. 9E, can include adjusting one or more parameters of the device (e.g., gain, configuration of the variable opacity elements) such that the light incident on the one or more light sensors can be within the operating range of the light sensors. With the adjusted parameters, physiological signals can be acquired (step 910 of process 900). The physiological signals can be used to compute the user's physiological information (step 912 of process 900). Methods for computing the physiological information can include noise or wavelength filtering steps, buffering and amplification of light signals of interest, and frequency spectrum analysis of light signals of interest (e.g., FT, DFT, FFT, and/or variants thereof).

Frequency spectrum analysis can include taking a FFT of the light signal to identify frequency peaks and passing the resulting frequency spectrum through a bandpass filter to determine the heart rate and breathing rate. For example, heart rate can be determined from signals in approximately the 0.5 Hz to 6 Hz frequency range, and the breathing rate can be determined from signals in approximately the 0.08 Hz to 1.5 Hz frequency range. Frequency spectrum analysis can be applied to broadband (e.g., a range of multiple wavelengths) light or can be applied to narrow band (e.g., one or more specific wavelengths) light. Examples of the disclosure can include using ambient light information for noise filtering of physiological signals such that systematic noise can be canceled.

Alternatively, if the ambient light levels do not meet a predetermined criteria (e.g., the ambient light levels are not greater than the predetermined threshold) (e.g., step 904 of process 900), then the device can be configured to perform one or more steps to conserve power, for example. The ambient light sensor and/or physiological data sensor can be turned off. In some examples, the controller can wait a predetermined time interval (e.g., 5 minutes) before checking whether the ambient light levels meet the predetermined criteria (e.g., the ambient light levels have increased to above the predetermined threshold). In some examples, the measured ambient light levels can be compared to a first predetermined threshold indicative of a low light environmental condition (e.g., step 908 of process 900) and a second predetermined threshold indicative of an ultra low light environmental condition. The ultra low light environmental condition can include turning off the ambient light sensor and/or physiological data sensor and checking the ambient light levels after a predetermined time.

FIG. 9B illustrates an exemplary method for switching the device to a bright light mode according to examples of the disclosure. The device can include one or more light sensors configured as an "ambient light sensor" and a "physiological data light sensor." The ambient light sensor can be configured to detect ambient light, and the physiological data light sensor can be configured to detect light that has interacted with the user's body. In some examples, the ambient light sensor and the physiological data light sensor can be the same light sensors (i.e., included in the same sensing unit). The device can also include a variable opacity element disposed over the ambient light and physiological data light sensors. The opacity of the variable opacity element can be increased (step 922 of process 920). The ambient light levels can be checked or measured using the ambient light sensor and/or physiological data light sensor (step 924 of process 920). The controller can compare the ambient light level to a predetermined threshold value (e.g., predetermined brightness level) (step 926 of process 920).

If the ambient light level meets the predetermined criteria (e.g., the ambient light level is greater than or equal to the predetermined threshold), then the gain of the physiological data light sensor can be reduced (step 928 of process 920). After the gain is reduced, the controller can determine whether the physiological signal is within a predetermined operating range (step 930 of process 920). In some examples, the predetermined operating range can include the operating range (e.g., the range between the noise floor and the saturation level) of the light sensor. In some examples, the operating range can include the fluctuating or periodic component of the light levels extending above the saturation level or dropping below the noise floor. In some examples, the predetermined operating range can include one or more properties of the physiological signal. For example, the shape of the physiological signal measured over a time interval may be indicative of low signal quality. In some examples, the signal-to-noise ratio (e.g., the intensity of the heart rate signal to the intensity of the motion noise) can be indicative of low signal quality. If the ambient light level is not greater than or equal to a predetermined brightness level, the physiological signal may be measured (step 934 of process 920) and the controller can determine whether the physiological signal is within a predetermined operating range (step 936 of process 920).

If the physiological signal is within the predetermined operating range, the physiological signals can be acquired (step 938 of process 920). In some examples, the acquired physiological signals can also be stored in memory (e.g., for future analysis). If the physiological signal is not within the predetermined operating range, the device can prompt the user to change to an environment with different lighting conditions (e.g., because the lighting conditions of the current environment can be too bright) (step 932 of process 920).

In some examples, the gain can be incrementally reduced to account for the bright light conditions, while keeping the gain within the operating range. Although the methods described above are discussed in the context of computation of heart rate and breathing rate using light information indicative of the user's blood flow, examples of the disclosure can include acquiring information and computing other physiologic characteristics. For example, methods and devices described herein can be used to generate PPG data based on light that has interacted with the skin, blood oxygenations, and/or body temperature of the user. The controller can determine whether the physiological signal is within a predetermined operating range (step 930 of process 920). If so, step 938 can be executed. If not, step 928 can be executed.

In some examples, the device may not include a variable opacity element coupled to the ambient light sensor. FIG. 9C illustrates an exemplary method for switching the device without a variable opacity element optically coupled to the ambient light sensor to a bright light mode according to examples of the disclosure. Optionally, the opacity of the variable opacity optically coupled to the physiological data light sensor can be increased (step 942 of process 940). The controller can determine whether the physiological signal (e.g., generated by physiological data light sensor) is within a predetermined operating range (e.g., operating range of the light sensor) (step 944 of process 940). If the physiological signal is not within the predetermined operating range, the gain of the physiological data light sensor can be reduced (step 946 of process 940). The controller can check/measure the physiological signal after reducing the gain (step 948 of process 940) and can determine whether the physiological signal is within a predetermined operating range (step 950 of process 940).

If the physiological signal is with predetermined operating range, the opacity of the variable opacity element can be changed (step 952 of process 940). If in any situation, the physiological signal is within the predetermined operating range (e.g., checked in step 944 and/or step 950) and/or the opacity of the variable opacity element has been changed (e.g., in step 952), the physiological signal can be acquired (step 954 of process 940).

In some examples, the device may not include any variable opacity element. FIG. 9D illustrates an exemplary method for switching the device without a variable opacity element to a bright light mode according to examples of the disclosure. The gain of the physiological data light sensor can be reduced (step 962 of process 960), and the physiological signals can be checked/measured (step 964 of process 960). The controller can determine whether the physiological signal is within a predetermined operating range (step 966 of process 960). If the device has a photochromic layer (step 968 of process 960), then the controller can wait one interval of time to allow the opacity to increase (step 970 of process 960). The physiological signal can then be checked/measured (step 972 of process 960). The controller can determine whether physiological signal is within a predetermined operating range (step 974 of process 960). If not, the controller can determine whether the opacity of the photochromic layer has reached its maximum and/or whether the maximum time has elapsed (step 976 of process 960). If neither the opacity has received its maximum nor the maximum time has elapsed, the controller can wait until either has occurred (e.g., to allow the photochromic layer to dark in response to the bright ambient light levels). If one of the maximum opacity or elapsed time has been reached, the controller can prompt the user to change the environment (step 978 of process 960). The device can prompt the user to change the environment. The physiological signal can be acquired and stored (step 980 of process 960). In some instances, the device may not have a photochromic layer (e.g., step 968 of process 960), so one or more of the steps 970-978 can be skipped.

FIG. 9E illustrates an exemplary method for switching the device to a low light mode according to examples of the disclosure. The device can include one or more light emitters positioned to illuminate the field-of-view of one or more light sensors. The one or more light sensors can include at least one physiological data light sensor. The gain of the physiological light sensors can be increased (step 984 of process 982). The physiological signals can be checked/measured (step 986 of process 982). The controller can determine whether the physiological signal (e.g., measured by the physiological data light sensor) is within a predetermined operating range (e.g., operating range of the light sensor) (step 988 of process 982).

If the physiological signal is not within a predetermined operating range, at least one of the one or more light emitters can be turned on (step 990 of process 982). In some examples, the device's battery levels may be low and/or the user may have set the device in a power saving (e.g., low power mode), so the controller may not activate the one or more lights sources (e.g., and instead can prompt the user to change the lighting conditions). In some examples, the activated one or more light emitters can be used to assist low levels of ambient light to achieve higher physiological signal levels. In some examples, the gain of the physiological light sensor can additionally be adjusted (e.g., reduced) to ensure that the physiological signal is within the predetermined operating range. The physiological signals can be checked with the assisted light emitters (step 991 of process 982), and the controller can determine whether the physiological signal is within a predetermined operating range (step 992 of process 982).

If the physiological signal is within a predetermined operating range, the physiological signals can be acquired and optionally stored (step 998 of process 982). If the physiological signal is not within a predetermined operating range, the controller can check whether the light emitter intensity is at its maximum limit (step 993 of process 982). If the light emitter intensity is at its maximum limit, the device can prompt the user to change the environment (e.g., to one with brighter light conditions because the environment is too dark) (step 994 of process 982). The physiological signal can be acquired and optionally stored in step 982. If the light emitter intensity is not at its maximum limit, the intensity of the light emitter can be increased (step 996 of process 982). The increase in intensity of the light emitter can be adjusted such that the detected physiological signals can be within the predetermined operating range by a predetermined margin. Optionally, the margin can be based on power conservation objectives. The physiological signals can be checked/measured with the adjusted light emitter intensity in step 991. In some examples, the gain can be incrementally increased to account for the low light conditions, while keeping the gain within the operating range.

Although the methods described above refer to acquiring light from an "ambient light sensor" and a "physiological data light sensor," it should be understood that these light sensors could be configured to measure any light regardless of its source. The above examples can further include using motion performance information from, for example, an accelerometer, instead of or in addition to, the ambient light sensor information. For example, motion artifacts (e.g., from the user's movement) can be included in the physiological signal(s) (e.g., as motion noise). To enhance the measurement accuracy, the controller can increase the signal-to-noise ratio by turning on the one or more light emitters in response to signals from the accelerometer. Additionally or alternatively, the controller can delay (e.g., wait 5 seconds or until the noise levels and/or accelerometer signals reduce) the measurement(s) from the physiological data light. In some examples, activating the one or more light emitters and/or delaying the measurements can be in response to variability (e.g., fluctuations) of the ambient light and/or accelerometer signals.

In some examples, the device can include one or more incident light angular acceptance elements. In some examples, the incident light angular acceptance element can be included in the variable opacity elements. The light incident on the light sensors can have differing angles of incidence. Light having some angles of incidence may include unwanted information, so selectively accepting (e.g., allowing the light to reach the light sensor) the light with unwanted information may be beneficial. The incident light angular acceptance element can be located proximate to one or more light sensors and can be electrically controlled via, e.g., the controller. The acceptance angle of the incident light angular acceptance element can adjust the acceptance angle of the incident light. In some instances, the adjustment of the acceptance angle can be based on which light sensor(s) (e.g., light sensor 412 or light sensor 414) is activated and/or which light sensor(s) are generating signals included in the determination of the user's physiological information. In this manner, the measurement accuracy may be enhanced.

A device is disclosed. The device can comprise: one or more first light sensors configured to measure light that has interacted with a user and generate a first signal indicative of the measured light; one or more second light sensors configured to measure ambient light and generate a second signal indicative of the measured ambient light; and logic configured to: receive the second signal, adjust a gain of the one or more first light sensors based on the second signal, receive the first signal, and determine one or more physiological information of the user based on the first signal. Additionally or alternatively, in some examples, the device further comprises: a display configured to display one or more images from a top surface of the device, wherein the one or more second light sensors are located at the top surface and the one or more first sensors are located at a bottom surface, opposite the top surface, of the device. Additionally or alternatively, in some examples, the one or more first light sensors and the one or more second light sensors are located on a same side of the device. Additionally or alternatively, in some examples, the one or more first light sensors are located on a bottom of the device and the one or more second light sensors are located on a sidewall of the device. Additionally or alternatively, in some examples, the one or more first light sensors and the one or more second light sensors are located in a same sensing unit. Additionally or alternatively, in some examples, the device further comprises: one or more light emitters configured to emit light when a level of the measured ambient light is less than a predetermined threshold. Additionally or alternatively, in some examples, the device further comprises: one or more light emitters configured to emit light when one or more characteristics of the first signal is outside a predetermined range. Additionally or alternatively, in some examples, the device further comprises: an accelerometer configured to measure an acceleration and generate an acceleration signal indicative of the measured acceleration, wherein the one or more light emitters are further configured to emit light based on the acceleration signal. Additionally or alternatively, in some examples, the device further comprises: one or more variable opacity elements optically coupled to the one or more first light sensors. Additionally or alternatively, in some examples, the device further comprises: one or more variable opacity elements optically coupled to the one or more second light sensors. Additionally or alternatively, in some examples, the device further comprises: one or more variable opacity elements operatively coupled to the logic, wherein the logic is further configured to: transmit a third signal to the one or more variable opacity elements, the third signal indicative of an opacity of the one or more variable opacity elements. Additionally or alternatively, in some examples, the device further comprises: one or more variable opacity elements, each variable opacity element including a plurality of regions, wherein each of the plurality of regions has different transmission properties. Additionally or alternatively, in some examples, the device further comprises: one or more variable opacity elements, each variable opacity element configured to select one or more wavelengths, different from other variable opacity elements, to allow to pass through. Additionally or alternatively, in some examples, the device further comprises: one or more variable opacity elements capable of moving in and out of a light path of the one or more first light sensors, one or more second light sensors, or both; and a motion system operatively coupled to the one or more variable opacity elements and the logic, wherein the logic is further configured to: transmit a third signal to the motion system, the third signal indicative of a motion state of the one or more variable opacity elements. Additionally or alternatively, in some examples, at least one of the one or more light sensors includes a plurality of detector pixels, the device further comprising: a color filter array including a plurality of color filter units, wherein each color filter unit is associated to one of the plurality of detector pixels. Additionally or alternatively, in some examples, the one or more first light sensors are configured with a first measurement frequency, and the one or more second light sensors are configured with a second measurement frequency, different from the first measurement frequency.

A method is disclosed. The method can comprise: detecting light that has interacted with a user using one or more light sensors; generating a first signal indicative of the detected light; detecting an ambient light; generating a second signal indicative of the detected ambient light; and adjusting a gain of the one or more light sensors based on the second signal. Additionally or alternatively, in some examples, adjusting the gain of the one or more light sensors includes: increasing the gain when a level of the detected ambient light is less than a predetermined threshold. Additionally or alternatively, in some examples, the predetermined threshold is a noise level. Additionally or alternatively, in some examples, adjusting the gain of the one or more light sensors includes: decreasing the gain when a level of the detected ambient light is greater than a predetermined threshold. Additionally or alternatively, in some examples, the predetermined threshold is a saturation limit. Additionally or alternatively, in some examples, the method further comprises: configuring the one or more light sensors to detect the ambient light. Additionally or alternatively, in some examples, the method further comprises: adjusting an opacity of one or more variable opacity elements based on the detected ambient light. Additionally or alternatively, in some examples, the adjusting includes selectively allowing one or more wavelengths to pass through the one or more variable opacity elements. Additionally or alternatively, in some examples, the one or more light sensors are configured to detect the same one or more wavelengths.

A method of detecting light that has interacted with a user using one or more light sensors is disclosed. The method can comprise: generating a first signal indicative of the detected light; detecting an ambient light having one or more characteristics; generating a second signal indicative of the detected ambient light; and when the one or more characteristics of the detected ambient light, the first signal, or both is outside a predetermined range, performing one or more of: emitting light using one or more light emitters, changing an opacity of a variable opacity element, excluding the first signal from a determination of one or more physiological signals of a user, and deactivating the one or more light sensors. Additionally or alternatively, in some examples, the method further comprises: adjusting one or more characteristics of the emitted light based on the detected ambient light. Additionally or alternatively, in some examples, the method further comprises: detecting an acceleration; emitting light using one or more light sources when the acceleration information meets a predetermined criteria; and deactivating the one or more light sources when the acceleration information does not meet a predetermined criteria. Additionally or alternatively, in some examples, the one or more characteristics of the detected ambient light include a frequency, the method further comprising: changing a measurement frequency of the one or more light sensors, wherein the measurement frequency is different from the frequency. Additionally or alternatively, in some examples, the one or more characteristics of the detected ambient light include a variability, the method further comprising: delaying the detection of light that has interacted with the user by a predetermined time. Additionally or alternatively, in some examples, the ambient light is associated with one or more first environmental periods and one or more second environmental periods, the one or more first environmental periods having a higher ambient light level than the one or more second environmental periods, and the predetermined range includes the one or more second environmental periods, the method further comprising: deactivating the one or more light emitters during the one or more first environmental periods. Additionally or alternatively, in some examples, the ambient light is associated with one or more first environmental periods and one or more second environmental periods, the one or more first environmental periods having a higher ambient light level than the one or more second environmental periods, and the predetermined range includes the one or more second environmental periods, the method further comprising: increasing the opacity of the variable opacity element during the one or more first environmental periods.

Although examples have been fully described with reference to the accompanying drawings, it is to be noted that various changes and modifications will become apparent to those skilled in the art. Such changes and modifications are to be understood as being included within the scope of the various examples as defined by the appended claims.

The invention claimed is:

1. A device comprising:
   a light emitter configured to emit first light;
   one or more first light sensors configured to measure second light that has interacted with a user and generate a first signal indicative of the measured second light;
   one or more second light sensors configured to measure ambient light and generate a second signal indicative of the measured ambient light;
   a variable opacity element optically coupled to the one or more first light sensors and configured to receive the second light; and
   a controller configured to:
      determine, based on the second signal, whether a light level of the measured ambient light is greater than or equal to a predetermined threshold;
      transmit a third signal to the variable opacity element, the third signal indicative of an opacity of the variable opacity element; and
      perform a measurement of physiological information based on the first signal, wherein:
      in accordance with a first determination that the light level of the measured ambient light is greater than or equal to the predetermined threshold, the second light is measured while the light emitter is not emitting light and the variable opacity element has a first opacity; and
      in accordance with a second determination that the light level of the measured ambient light is less than the predetermined threshold, the second light is measured while the light emitter is emitting the first light and the variable opacity element has a second opacity less than the first opacity.

2. The device of claim 1, further comprising:
   a display configured to display one or more images from a first surface of the device, wherein the one or more second light sensors are located at the first surface and the one or more first sensors are located at a second surface, opposite the first surface, of the device.

3. The device of claim 1, wherein the one or more first light sensors and the one or more second light sensors are located on a same side of the device.

4. The device of claim 1, wherein the one or more first light sensors are located on a bottom of the device and the one or more second light sensors are located on a sidewall of the device.

5. The device of claim 1, wherein the variable opacity element includes a plurality of regions, wherein the plurality of regions have different transmission properties.

6. The device of claim 1, wherein:
   the variable opacity element is capable of moving in and out of a light path of the one or more first light sensors, the one or more second light sensors, or both; and
   a motion system operatively coupled to the variable opacity element and the controller, wherein the controller is further configured to:
   transmit a fourth signal to the motion system, the fourth signal indicative of a motion state of the variable opacity element.

7. The device of claim 1, further comprising:
   at least one angular acceptance element,
   wherein the controller is further configured to determine which of the one or more first or second lights sensors are activated.

8. The device of claim 7, wherein:
   the variable opacity element and the at least one angular acceptance element are integrated;
   the at least one angular acceptance element is capable of being electrically controlled,
   wherein the controller is further configured to adjust an acceptance angle of the at least one angular acceptance element based on which of the one or more first light sensors or the one or more second light sensors are activated.

9. The device of claim 1, wherein at least one of the one or more first light sensors or the one or more second light sensors includes a plurality of detector pixels, the device further comprising:
   a color filter array including a plurality of color filter units, wherein each color filter unit is associated to one of the plurality of detector pixels.

10. The device of claim 1, wherein the one or more first light sensors are configured with a first measurement frequency, and the one or more second light sensors are configured with a second measurement frequency, different from the first measurement frequency.

11. The device of claim 1, wherein the variable opacity element is adapted to be positioned between the user and the one or more first light sensors.

12. The device of claim 1, wherein:
    the variable opacity element is a first variable opacity element; and
    the device further comprises a second variable opacity element optically coupled to the one or more second light sensors.

13. The device of claim 12, wherein the second variable opacity element is further optically coupled to the one or more first light sensors.

14. A method comprising:
    utilizing a device including a variable opacity element coupled to one or more first light sensors, wherein the variable opacity element is configured to receive light that has interacted with a user and is controlled by a controller configured to transmit a first signal to the variable opacity element, the first signal indicative of an opacity of the variable opacity element;
    detecting ambient light using one or more second light sensors;
    generating a second signal indicative of the detected ambient light;
    determining, based on the second signal, whether a light level of the ambient light is greater than or equal to a predetermined threshold;
    in accordance with a first determination that the light level of the ambient light is greater than or equal to the predetermined threshold, detecting, while a light emitter is not emitting light and the variable opacity element has a first opacity, first light that has interacted with the user using the one or more first light sensors;

in accordance with a second determination that the light level of the ambient light is less than the predetermined threshold:
  emitting second light using the light emitter; and
  detecting the first light while the light emitter is emitting the second light and the variable opacity element has a second opacity less than the first opacity;
generating a first light signal indicative of the detected first light; and
performing a measurement of physiological information based on the first light signal indicative of the detected first light.

15. The method of claim 14, further comprising:
adjusting the first or second opacity of the variable opacity element based on the detected ambient light.

* * * * *